United States Patent
Goldfain et al.

(10) Patent No.: US 11,457,802 B2
(45) Date of Patent: Oct. 4, 2022

(54) BORESCOPIC OPTICAL SYSTEM FOR MEDICAL DIAGNOSTIC INSTRUMENTS AND MEDICAL DIAGNOSTIC INSTRUMENTS HAVING INTERLOCKING ASSEMBLY FEATURES

(71) Applicant: Welch Allyn, Inc., Skaneateles Falls, NY (US)

(72) Inventors: Ervin Goldfain, Syracuse, NY (US); Raymond A. Lia, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 325 days.

(21) Appl. No.: 16/779,728

(22) Filed: Feb. 3, 2020

(65) Prior Publication Data
US 2020/0170496 A1   Jun. 4, 2020

Related U.S. Application Data

(63) Continuation of application No. 16/016,757, filed on Jun. 25, 2018, now Pat. No. 10,548,468, which is a
(Continued)

(51) Int. Cl.
*A61B 1/227* (2006.01)
*A61B 3/12* (2006.01)
(Continued)

(52) U.S. Cl.
CPC .............. *A61B 1/227* (2013.01); *A61B 1/06* (2013.01); *A61B 3/0008* (2013.01); *A61B 3/12* (2013.01);
(Continued)

(58) Field of Classification Search
CPC ......... A61B 1/227; A61B 1/06; A61B 3/0008; A61B 3/12; A61B 3/1208; A61B 3/156; G02B 13/0095
(Continued)

(56) References Cited

U.S. PATENT DOCUMENTS

| 3,586,424 | A | 6/1971 | Schenk et al. |
| 3,698,387 | A | 10/1972 | Moore et al. |

(Continued)

FOREIGN PATENT DOCUMENTS

| EP | 1 694 195 B1 | 4/2009 |
| WO | WO 2005/020804 A1 | 3/2005 |
| WO | WO 2005/044098 A1 | 5/2005 |

OTHER PUBLICATIONS

European Office Action for EP 15 771 386.8; dated Aug. 3, 2018; 2 pgs.
(Continued)

*Primary Examiner* — Mohammed A Hasan
(74) *Attorney, Agent, or Firm* — Barclay Damon LLP

(57) ABSTRACT

A medical diagnostic instrument or a plurality of disparate medical diagnostic instruments are configured with a common optical architecture that functionally creates a virtual eye to create closer proximity to a patient and therefore increase the field of view in regard to a target of interest. The optical system includes a distal optical element, at least one relay lens and an eyepiece lens in which the optical system can be integrated within at least one instrument or be provided using a releasable module. Additionally, at least one of a viewing assembly and illumination assembly of at least one medical diagnostic instrument can be assembled using a series of components that are connected by interlocking features.

17 Claims, 38 Drawing Sheets

Related U.S. Application Data continuation of application No. 15/493,500, filed on Apr. 21, 2017, now Pat. No. 10,028,648, which is a continuation of application No. 14/853,282, filed on Sep. 14, 2015, now Pat. No. 9,675,246.

(60) Provisional application No. 62/071,128, filed on Sep. 15, 2014.

(51) Int. Cl.
  *G02B 13/00* (2006.01)
  *A61B 3/00* (2006.01)
  *A61B 3/15* (2006.01)
  *A61B 1/06* (2006.01)

(52) U.S. Cl.
  CPC ............ *A61B 3/1208* (2013.01); *A61B 3/156* (2013.01); *G02B 13/0095* (2013.01)

(58) Field of Classification Search
  USPC .................................................. 351/222, 221
  See application file for complete search history.

(56) References Cited

U.S. PATENT DOCUMENTS

| | | | |
|---|---|---|---|
| 3,914,032 A | 10/1975 | Takano | A61B 3/14 |
| | | | 351/205 |
| 3,978,850 A | 9/1976 | Moore et al. | |
| 4,526,449 A | 7/1985 | Newman et al. | |
| 5,658,235 A | 8/1997 | Priest et al. | |
| 7,354,399 B2 | 4/2008 | Strom | A61B 1/227 |
| | | | 600/200 |
| 7,364,297 B2 | 4/2008 | Goldfain et al. | |
| 7,399,275 B2 | 7/2008 | Goldfain et al. | |
| 8,066,634 B2 | 11/2011 | Andreassen et al. | |
| 8,197,403 B2 | 6/2012 | Strom et al. | |
| 8,602,971 B2 | 12/2013 | Farr | |
| 9,445,713 B2 | 9/2016 | Douglas | A61B 1/00009 |
| 10,028,648 B2 | 7/2018 | Goldfain | A61B 3/12 |
| 2005/0110949 A1* | 5/2005 | Goldfain | A61B 3/158 |
| | | | 351/206 |
| 2006/0077345 A1* | 4/2006 | Burrows | A61B 3/156 |
| | | | 351/207 |
| 2008/0309876 A1 | 12/2008 | Massie | A61B 3/12 |
| | | | 351/219 |
| 2010/0081875 A1 | 4/2010 | Fowler et al. | |
| 2010/0317924 A1 | 12/2010 | Sisko et al. | |
| 2012/0209074 A1 | 8/2012 | Titus | |
| 2012/0320340 A1 | 12/2012 | Coleman, III | |
| 2013/0128223 A1* | 5/2013 | Wood | A61B 1/00039 |
| | | | 351/246 |
| 2013/0178707 A1 | 7/2013 | Kwong | |
| 2013/0208241 A1 | 8/2013 | Lawson et al. | |
| 2013/0267783 A1* | 10/2013 | Davis | A61B 1/227 |
| | | | 600/199 |
| 2014/0146288 A1 | 5/2014 | Anand et al. | |
| 2015/0103317 A1* | 4/2015 | Goldfain | A61B 3/14 |
| | | | 351/207 |
| 2016/0073875 A1* | 3/2016 | Goldfain | A61B 3/0008 |
| | | | 351/205 |

OTHER PUBLICATIONS

European Office Action for EP 15 771 386.8; dated Mar. 20, 2019; 3 pgs.

European Examination Report for EP 15 771 386.8; dated Sep. 16, 2019; 2 pgs.

International Preliminary Report on Patentability and Written Opinion; dated Mar. 21, 2017; 8 pages.

Large Field of View, Modular, Stabilized, Adaptive-Optics-Based Scanning Laser Ophthalmoscope; Stephen A. Burns, Remy Tumbar and Ann E. Eisner; http://www.ncbi.nlm.nih.gov/pmc/articles/PMC2443858/pdf/nihms21600; Published in May 2007; 24 pages.

Adaptive Optics Scanning Laser Ophthalmoscope With Integrated Wide-Field Retinal Imaging and Tracking: R. Daniel Ferguson, Zhangyi Zhong, Daniel X. Hammer, Mircea Mujat, Ankit H. Patel, Cong Deng, Weiyao Zou and Stephen A. Burns; http://www.ncbi.nlm.nih.gov/pmc/articles/PMC3071649/pdf/nihnis-250025; Published in Nov. 2010; 27 pages.

Invitation to Pay Additional Fees, and Where Applicable, Protest Fee; dated Dec. 2, 2015: 6 pages.

European Search Report for EP 21 208 704.3; dated Jan. 24, 2022; 7 pages.

* cited by examiner

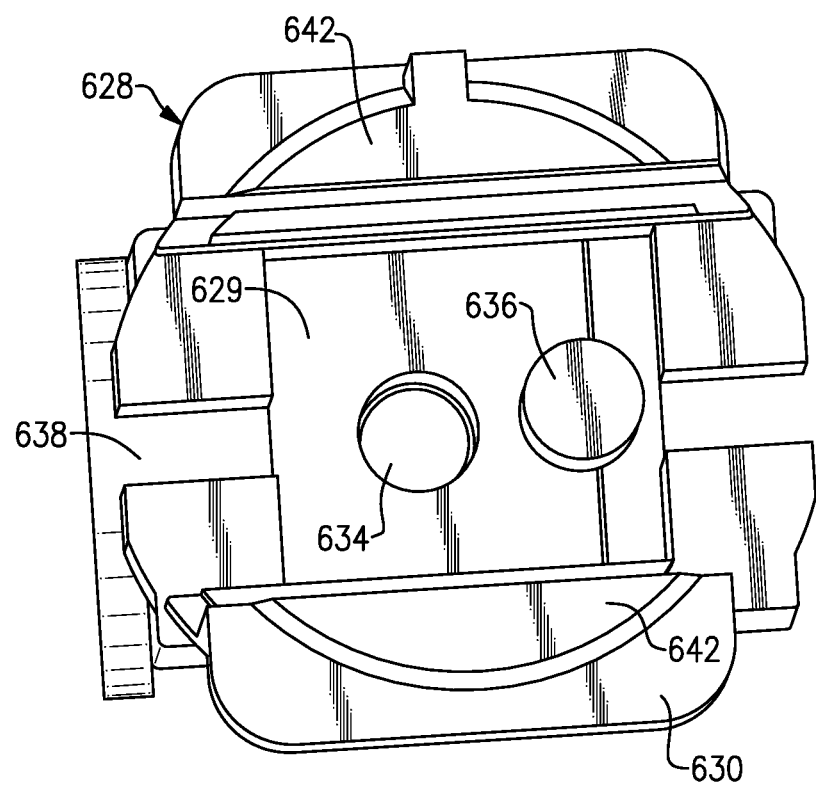
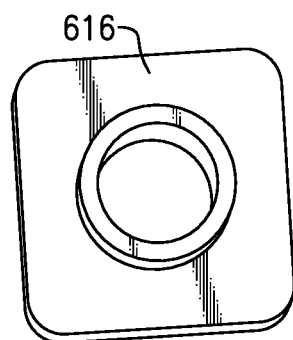
FIG.7(c)

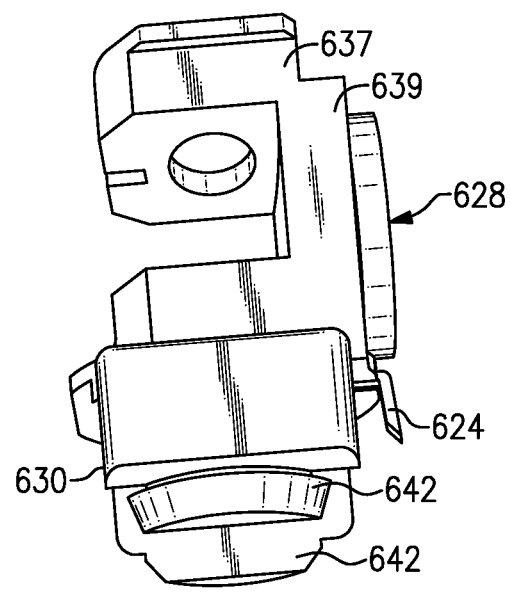
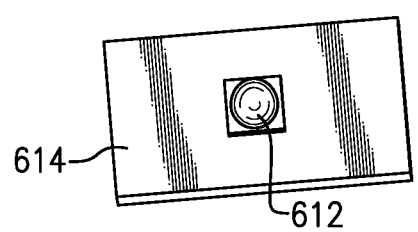
FIG.7(d)

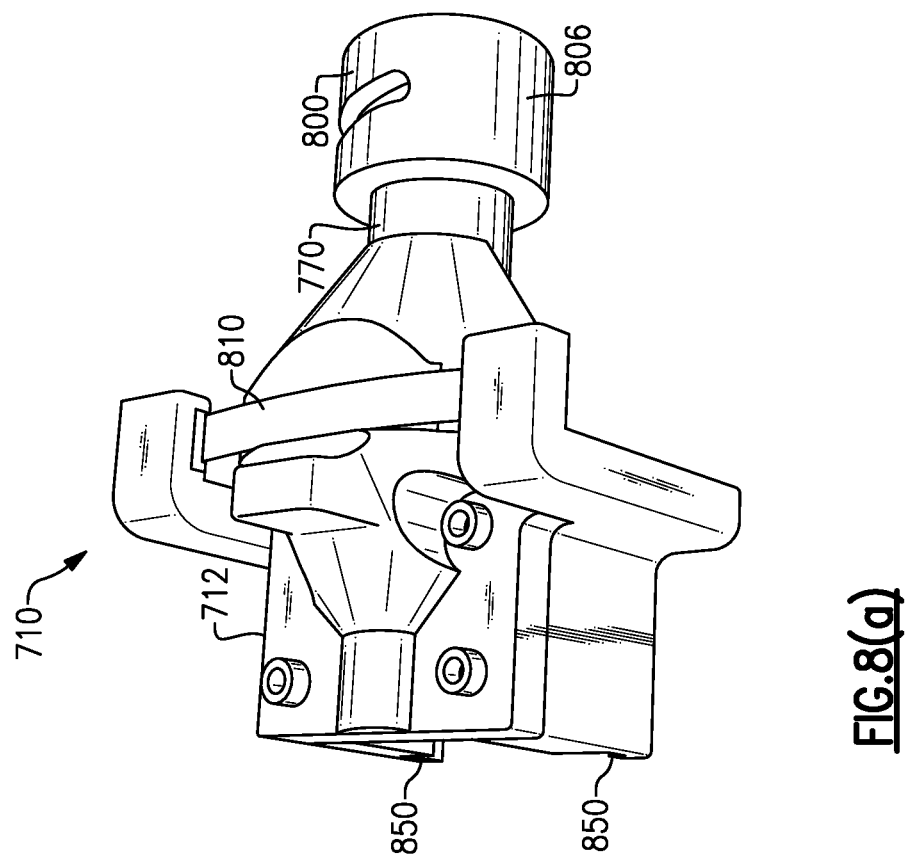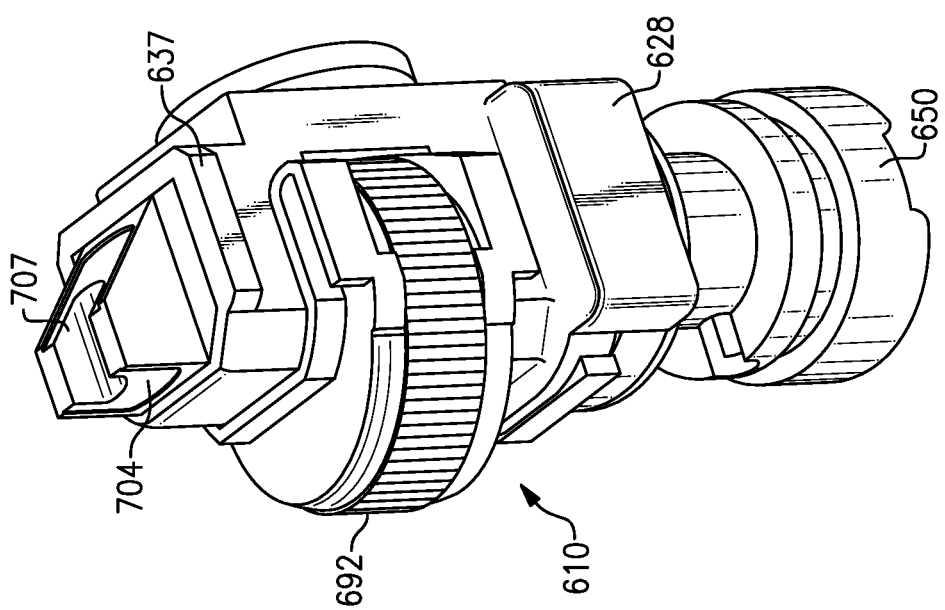

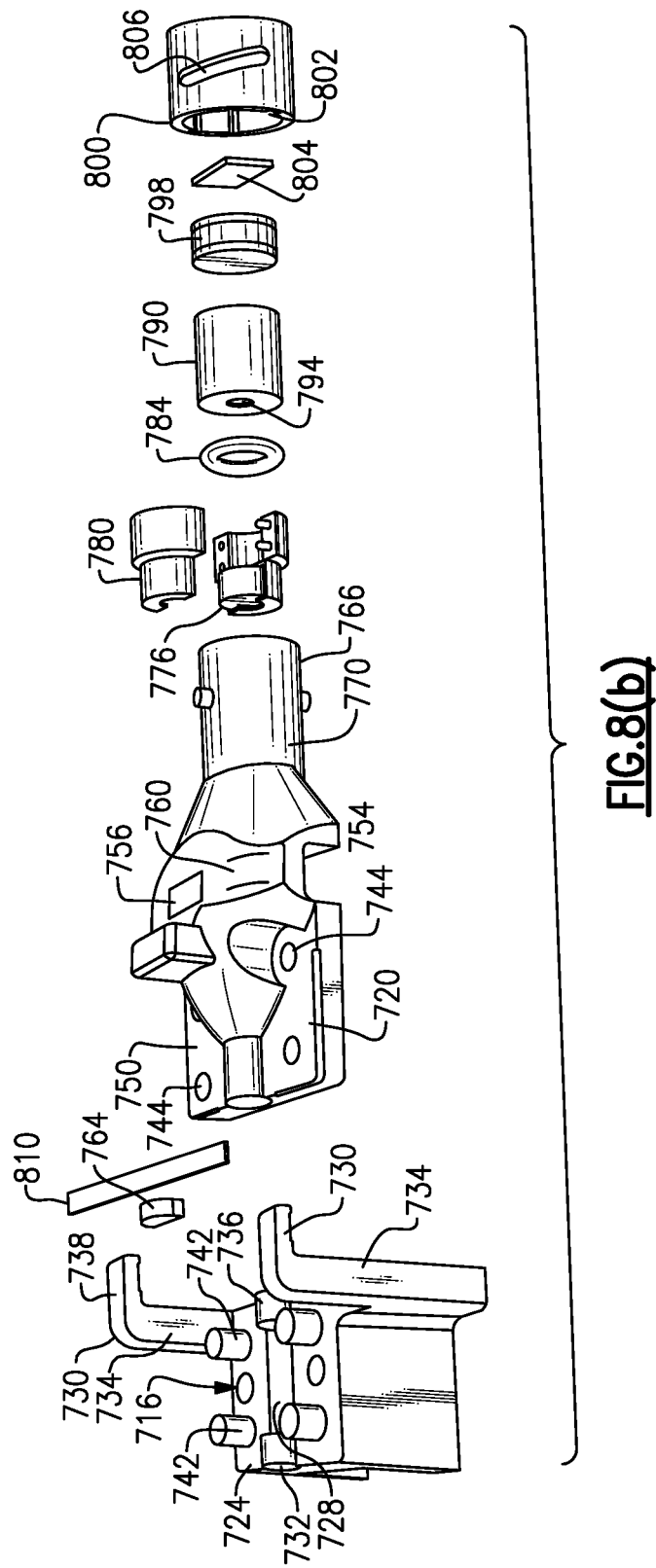

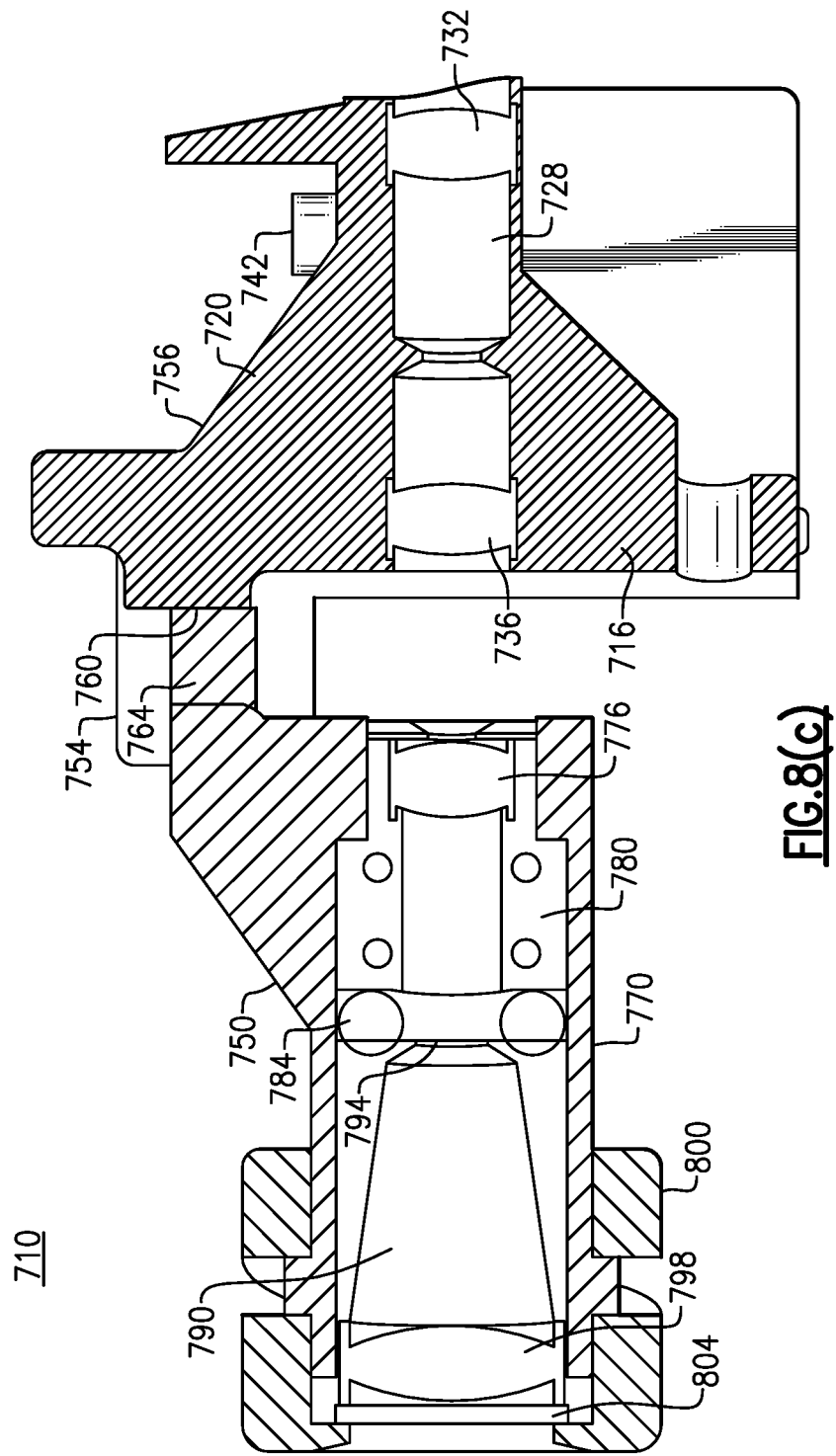

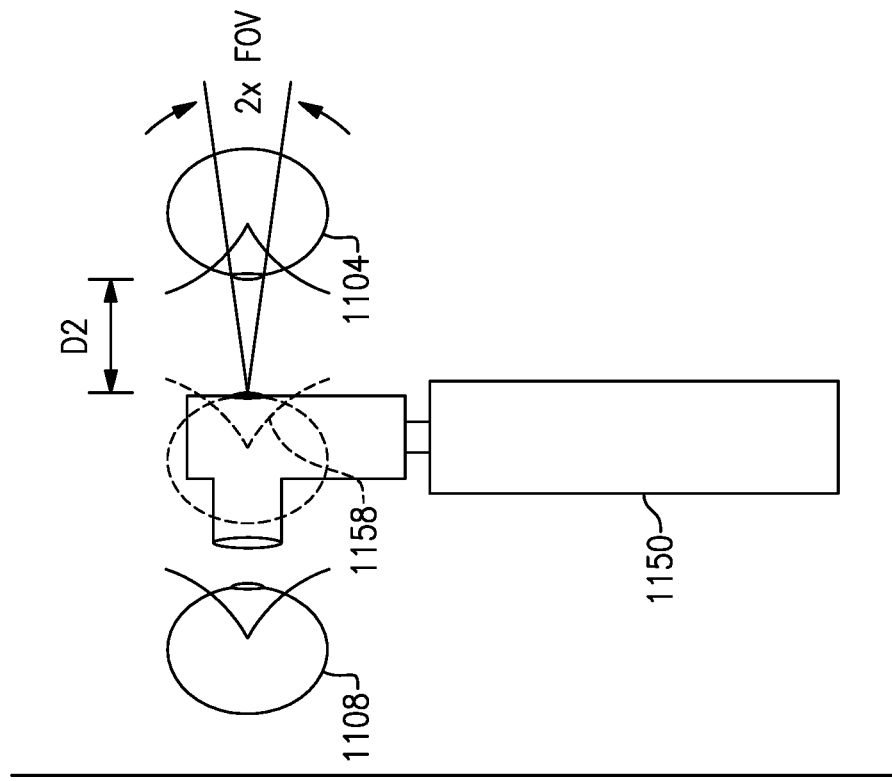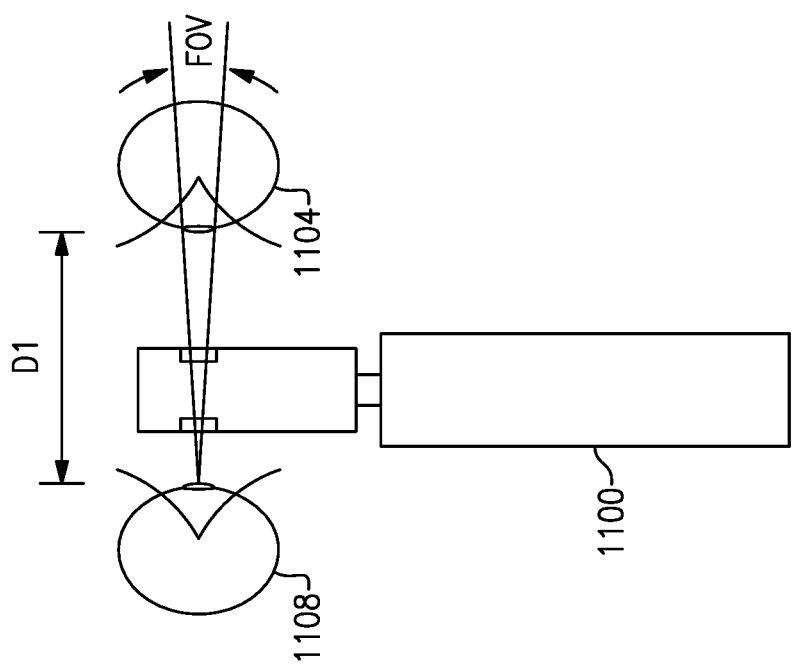
FIG. 14

BORESCOPIC OPTICAL SYSTEM FOR MEDICAL DIAGNOSTIC INSTRUMENTS AND MEDICAL DIAGNOSTIC INSTRUMENTS HAVING INTERLOCKING ASSEMBLY FEATURES

CROSS REFERENCE TO RELATED APPLICATIONS

This application is a continuation of and claims priority to U.S. patent application Ser. No. 16/016,757, entitled Borescopic Optical System for Medical Diagnostic Instruments and Medical Diagnostic Instruments Having Interlocking Assembly Features, filed June 25, 2018, which is a continuation of and claims priority to U.S. patent application Ser. No. 15/493,500, entitled Borescopic Optical System for Medical Diagnostic Instruments and Medical Diagnostic Instruments Having Interlocking Assembly Features, filed Apr. 21, 2017 (now U.S. Pat. No. 10,028,648), which is a continuation of and claims priority to U.S. patent application Ser. No. 14/853,282, entitled Borescopic Optical System for Medical Diagnostic Instruments and Medical Diagnostic Instruments Having Interlocking Assembly Features, filed Sep. 14, 2015 (now U.S. Pat. No. 9,675,246), which claims priority to U.S. patent application Ser. No. 62/071,128, entitled Borescopic Optical System for Medical Diagnostic Instruments and Medical Diagnostic Instruments Having Interlocking Assembly Features, filed Sep. 15, 2014, pursuant to relevant portions of 35 U.S.C. § 120 and 37 CFR § 1.53, the entire contents of each listed document being incorporated herein by reference.

TECHNICAL FIELD

This application relates generally to the field of diagnostic medicine and more specifically to a medical diagnostic instrument having an enhanced field of view, as well as an optical architecture that can be commonly shared by a suite of disparate diagnostic instruments.

BACKGROUND

Certain instruments are well known in the medical field for conducting physical assessments of patients and in which separate instruments are used for examining specific target areas. For example, ophthalmoscopes are used by a primary physician or ophthalmologist for examining the eyes, otoscopes are utilized for examining the ear canal and tympanic membrane, and laryngoscopes are used for examining the throat passage.

A general pervasive issue with these physical assessment devices is in providing a suitably large field of view of the intended target of interest. For example, it is desirable and advantageous to be able to access the entire tympanic membrane while using an otoscope. It is further desirable to be able to capture more of the retinal area of the eye all at once during an examination.

An issue in creating a larger field of view is that of the instrument itself. For example and with ophthalmoscopes, the field of view can be expanded by shortening the working distance between the patient and the instrument. The foregoing, however, creates issues in terms of anxiety and discomfort for the patient. It is therefore desirable to provide a medical diagnostic instrument that can provide a larger field of view, but without having to shorten the working distance between the instrument and the patient.

Yet another pervasive issue in the field relates to improving manufacturability of such diagnostic instruments in order to reduce labor and associated material costs by using a minimum number of components, but without sacrificing reliability. To better deal with this concern, it would be extremely beneficial to develop a suitable optical architecture that could be shared between multiple types of physical assessment devices and to develop a simpler manufacturing method for these devices.

BRIEF DESCRIPTION

According to one aspect, there is provided a medical diagnostic instrument configured for viewing a target of interest, the instrument comprising an instrument housing having a distal end, an opposing proximal end and an interior. An optical system that is disposed within the interior of the instrument housing comprises a distal objective lens, at least one intermediately disposed relay lens and a proximal eyepiece lens. Each of the lenses are commonly disposed along an optical axis, in which the optical system is configured to create an entrance pupil distal of the distal end of the instrument in order to create an increased field of view of the target of interest. According to at least one embodiment, the instrument is an ophthalmoscope.

In a preferred version, the herein described optical system creates an entrance pupil that is distal of the instrument housing. This entrance pupil establishes a "virtual eye" of the caregiver that increases the working distance and the field of view by effectively shifting the eye of the caregiver away from the patient's eye. The optical elements used for purpose of this system can be defined by a plastic molded design in which each of the optical elements are reversible/symmetrical and corrected for optical aberrations by means of aspheric curves. According to at least one embodiment, each of the lenses include a raised peripheral edge to protect the lenses from surface damage. At least one field stop can be provided for minimizing glare or unwanted light from the system.

The optical system can be disposed within a viewing assembly that includes features that enable interlocking connection with the illumination assembly.

In at least one embodiment, the optical system can be integrated as part of the instrument. In one version, a module equipped with the above optical system can be releasably attached to the medical diagnostic instrument to create the entrance pupil and also thereby increase the field of view.

According to yet another aspect, an otoscope is provided that comprises an instrument head having a distal end opening, an opposing proximal end opening and a substantially hollow interior enabling a target of interest to be viewed by a caregiver in a first mode. A module is releasably attachable for insertion into the interior of the instrument head, the module having an optical system that increases the field of view for viewing a target of interest in a second mode.

According to at least embodiment, the module comprises a distal optical element, at least one intermediate relay lens element and a proximal eyepiece lens element, each of the lens elements being aligned with the distal and proximal end openings of the instrument head when attached. The instrument head can include a proximal window that is releasably removable to permit inclusion of the module.

In at least one embodiment, each of the lens elements of the module are made from a molded plastic, wherein each of the lens elements of the module are symmetric and reversible. In at least one version, each of the lens elements in the optical system are interchangeable. According to at least one embodiment, each of the lens elements can further include a raised peripheral edge along each optical surface thereof to minimize damage during handling and assembly.

The at least one relay lens and eyepiece lens element can be axially disposed in relation to at least one flexible member within a module housing, the module further including a twistable retaining cap that can permit minor positional adjustments of the lens elements to effect minor focus adjustments.

According to another aspect, a plurality of medical diagnostic instruments are provided wherein each of the medical diagnostic instruments include an optical system that is configured to produce a virtual pupil at the distal end of the instrument in order to increase the field of view. The plurality of instruments may include an otoscope and an ophthalmoscope, among others.

In one embodiment, the optical system can be integrated within at least one instrument housing. In another version, a module having the optical system can be releasably attached to at least one of the medical diagnostic instruments.

The optical system can include an objective distal lens, at least one intermediate relay lens and a proximal eyepiece lens, each of the lenses being commonly disposed along an optical axis of the instrument. In one version, each of the lenses of the optical system comprise symmetric reversible optical surfaces. In a preferred version, the lenses can be made from a moldable plastic in which each side of the lens can include a raised peripheral edge that can act in order to minimize damage to the optical surfaces during handling thereof in assembly.

In at least one embodiment, at least one of the medical diagnostic instruments further comprises an illumination assembly and in which the optical system and the illumination assembly can include features to enable an interlocking connection therebetween. In at least one version, the illumination assembly can include a plurality of components having respective features to enable interlocking connection therebetween.

The instruments having the common optical system can include ophthalmoscopes and otoscopes, among others. The optical system can include at least one distal optical element and at least one pair of relay lenses commonly disposed along an optical axis of the instrument and wherein the optical system is configured to create an entrance pupil that is distal of the distal end of the instrument housing in order to create the expanded field of view.

According to yet another aspect, a method is provided for manufacturing a medical diagnostic instrument to increase the effective field of view of the instrument. The method comprises providing an optical system in the instrument, the optical system having at least a distal objective lens, at least one intermediate relay lens and a proximal eyepiece lens in which the optical system is configured to create an entrance pupil distal of a distal end of the instrument.

In one version, each of the lenses of the optical system can be symmetric and reversible. According to one embodiment, the lenses can include a raised peripheral edge along each optical surface that can minimize damage while handling during assembly. In one version, the lenses can be made from plastic.

The medical diagnostic instrument can be at least one of an ophthalmoscope and an otoscope. According to one version, the optical system is provided as a module to an existing medical diagnostic instrument, such as an otoscope, the method further including the step of providing the module for inclusion into the interior of the instrument following removing of a releasable proximal window of the instrument. As such, the otoscope can then be configured to operate in separate modes depending on the inclusion of the releasably attachable module; namely, a first mode that enables the inclusion of tools within the interior of the otoscope, and a second enhanced field of view mode that includes the module.

According to yet another aspect, there is provided an optical module for placement within a medical diagnostic instrument to increase the effective field of view with respect to a target of interest, the module comprising a module housing including at least one distal optical element and at least one pair of relay lenses disposed within an interior of the housing and aligned commonly along an optical axis and wherein the optical system forms an entrance pupil distal of the distal end of the module to create an entrance pupil.

According to yet another aspect, there is provided a physical assessment device comprising an instrument housing having an interior, a viewing assembly disposed between distal and proximal end openings of the instrument housing, and an illumination assembly including at least one light source for illuminating a target of interest. According to this aspect, at least one of the viewing assembly and illumination assembly can have a plurality of components that are assembled by means of interlocking engagement. According to at least one embodiment, the illumination assembly and viewing assembly can include interlocking features that enable releasable connection therebetween.

According to one version, the illumination assembly can be configured for interlocking connection with a first viewing assembly having a first field of view and a second viewing assembly having a second field of view in which one of the viewing assemblies produces a distal entrance pupil for providing an enhanced field of view of an intended target of interest. In one version, the viewing assembly can be provided with a borescopic optical system comprising a distal objective lens, at least one intermediate relay lens, and a proximal eyepiece lens. The instrument can, for example, be an ophthalmoscope.

In one embodiment, each of the lenses used in the optical system are symmetrical and reversible, enabling the lenses to be easily assembled and without creating manufacturing errors. To further prevent damage to optical surfaces, the lenses can include a raised peripheral edge on each optical surface.

One advantage realized herein is that of modularization which can provide a common optical architecture for a number of disparate medical diagnostic instruments.

Another advantage is that the optical adapter when attached to a medical instrument, such as an otoscope, can further permit access of an intended target by tools, as needed.

Yet another advantage is that an enhanced field of view as provided by the herein described optical system permits more reliable and comprehensive examinations of a patient to be conducted.

Still another advantage realized is that of faster diagnostic patient examinations in that the realized enhanced field of view permits easier navigation by the caregiver of a larger target area in order to find the intended point of interest and to pan the instrument.

Additionally and through the virtual pupil that is created, the target of interest is actually made closer which provides more magnification, thereby making it considerably easier for the caregiver to discern features of the intended medical target.

These and other features and advantages will be readily apparent from the following Detailed Description, which should be read in conjunction with the accompanying drawings.

BRIEF DESCRIPTION OF THE DRAWINGS

FIG. 7(a)-7(k) depicts sequential partial assembly views of a portion of the medical diagnostic instrument of FIG. 6;

FIGS. 8(a)-(f) depict sequential partial assembly views of an optical assembly for a medical diagnostic instrument made in accordance with an embodiment, including a sectioned view of an optical system which is shown in FIG. 8(c);

FIG. 14 is a schematic depiction comparing a prior direct ophthalmoscope with an instrument configured with an optical system in accordance with an embodiment.

DETAILED DESCRIPTION

The following relates to various embodiments of physical assessment devices or instruments as well as components that are engageable therewith, each of which can be configured with a common optical architecture that permits an enhanced field of view of a medical target of interest. More specifically, the description relates to embodiments that are directed to optical otoscopes and ophthalmoscopes. It will be readily understood that the concepts discussed herein may be applicable to other physical assessment devices, including versions of digitally configured devices employing electronic imagers or devices. In addition and throughout this description, several terms are often used in order to provide a suitable frame of reference with regard to the accompanying drawings. These terms, which include "exterior", "interior", "distal", "proximal", "inner", "outer" and the like are not intended to limit the scope of the concepts which are discussed and claimed herein, except in those instances where so specifically indicated.

Figure 1A:
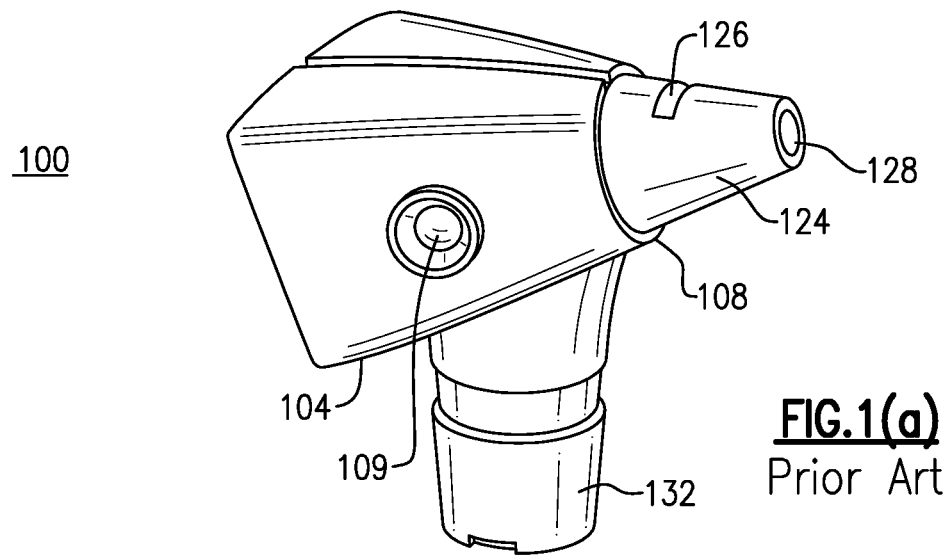
FIG. 1(a) is a side perspective view of a prior art medical diagnostic instrument and more specifically, an otoscope.
Figure 1B:
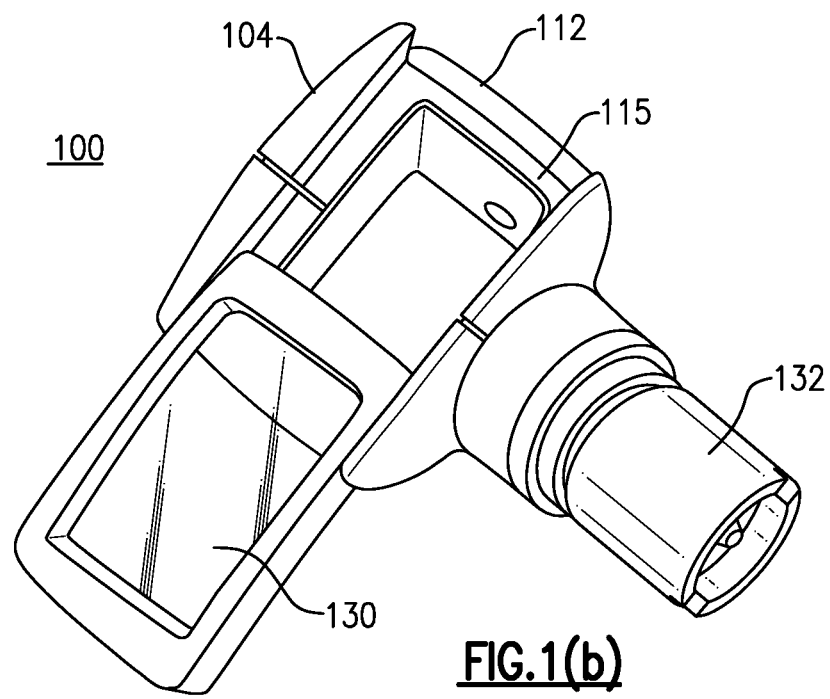
FIG. 1(b) is a rear perspective view of the prior art otoscope of FIG. 1(a)

For purposes of background and referring to FIGS. 1(a) and 1(b), a typically known otoscope 100 is defined by an instrument head 104 having a distal end 108 and an opposing proximal end 112, which further defines a hollow interior 115. An axisymmetric speculum tip element (not shown) can be releasably attached, typically by means of a bayonet-type connection, in overlaying relation onto a truncated frusto-conical insertion portion 124 disposed at the distal end 108 of the instrument head 104. The distal insertion portion 124 includes a slot 126 for releasably engaging an interior feature of the speculum tip element, as well as a distal opening 128 that is aligned with the distal opening of the speculum tip element. When attached to the instrument 100 and in use, the speculum tip element is configured to be placed up to a predetermined distance into the ear canal of a patient.

The caregiver observes the ear canal through a magnifying optic or window 130 that is provided at the proximal end 112 of the instrument head 104. The instrument head 104 is supported by a handle (not shown) that includes at least one rechargeable battery configured to electrically power a contained light source, typically an incandescent or halogen bulb, that is disposed at an upper end of the instrument handle. A lower portion of the instrument head 104 includes a contact disposed in a bayonet connector 132. A polished proximal end of the bundle of optical fibers (not shown) is optically coupled to the light source with the opposing ends encircling the interior of the distal end of the insertion portion 124 to create uniform illumination. An adjustment control, such as a rheostat (not shown), is further provided in order to control the level of illumination. In use, this instrument 100 is configured to have a field of view of approximately 15 degrees, while the diameter of the average tympanic membrane is approximately 7 mm. Details relating to the design and operation of this medical diagnostic instrument, including the attachment to the handle are provided in U.S. Pat. Nos. 3,698,387 and 3,978,850, the entire contents of which are herein incorporated by reference.

Figure 2A:
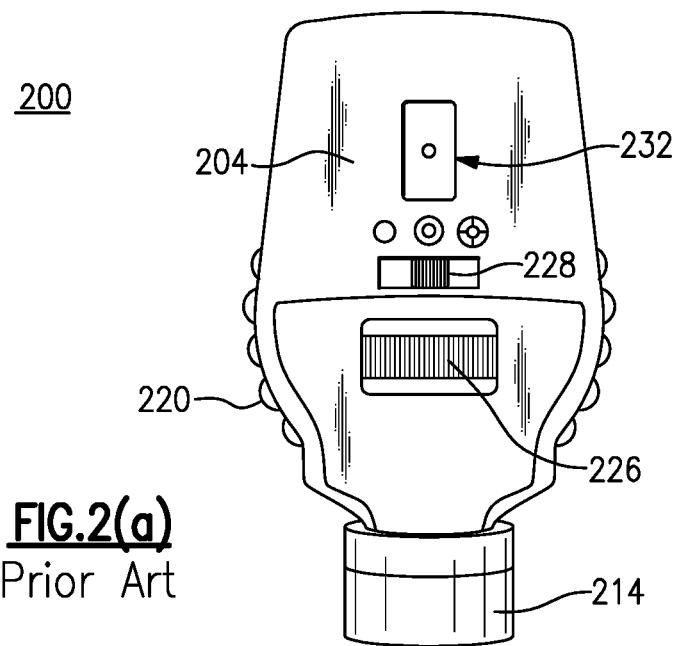
FIG. 2(a) is a front view of another prior art medical diagnostic instrument and more specifically, an ophthalmoscope.
Figure 2B:
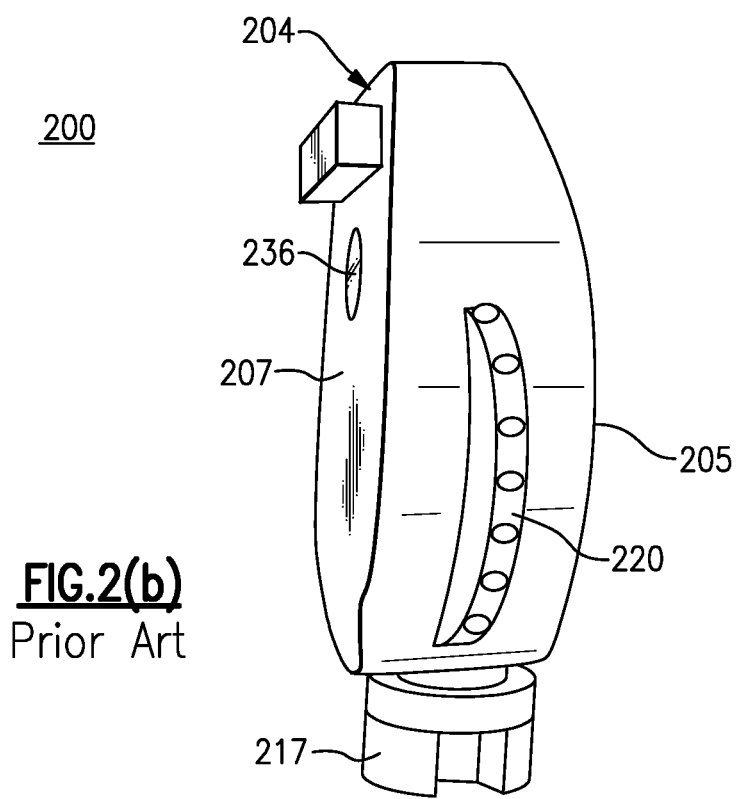
FIG. 2(b) is a side elevational view of the ophthalmoscope of FIG. 2(a)

With reference to FIGS. 2(a) and 2(b), a known optical ophthalmoscope 200 typically includes an instrument head 204 that includes a distal end 205 and an opposing proximal end 207, the instrument head 204 being supported to and connected through a bayonet connector 214 to an instrument handle (not shown) that contains at least one rechargeable battery connected to a light source provided in the upper end of the handle. As in the case of the otoscope 100, FIG. 1, one polished end of a bundle of optical fibers are optically coupled to the contained light source and the opposing end of the fiber bundle encircles the interior of a distal opening of the instrument head 204 in order to direct illumination toward the target of interest (eye). A diopter wheel 220 is disposed for rotational movement relative to an optical axis of the instrument 200, in which the caregiver can view portions of the eye through an aligned opening 232, 236 provided in the proximal and distal ends 207, 205 of the instrument 200, as well as an aperture wheel 226. The instrument 200 further includes a sliding polarizer red/free switch 228 beneath the opening 232.

Moving the instrument 200 closer to the patient will increase the field of view, but patients are made anxious when the instrument 200 is brought into immediate proximity with the eye, and as a result these instruments 200 are typically used at an appropriate working distance (approximately 13-15 mm) between the patient and the instrument with the instrument having a field of view of approximately 5 degrees. Details relating to the workings, design and operation of this instrument are known found in U.S. Pat. No. 4,526,449, the entire contents of which are herein incorporated by reference.

Figure 3:
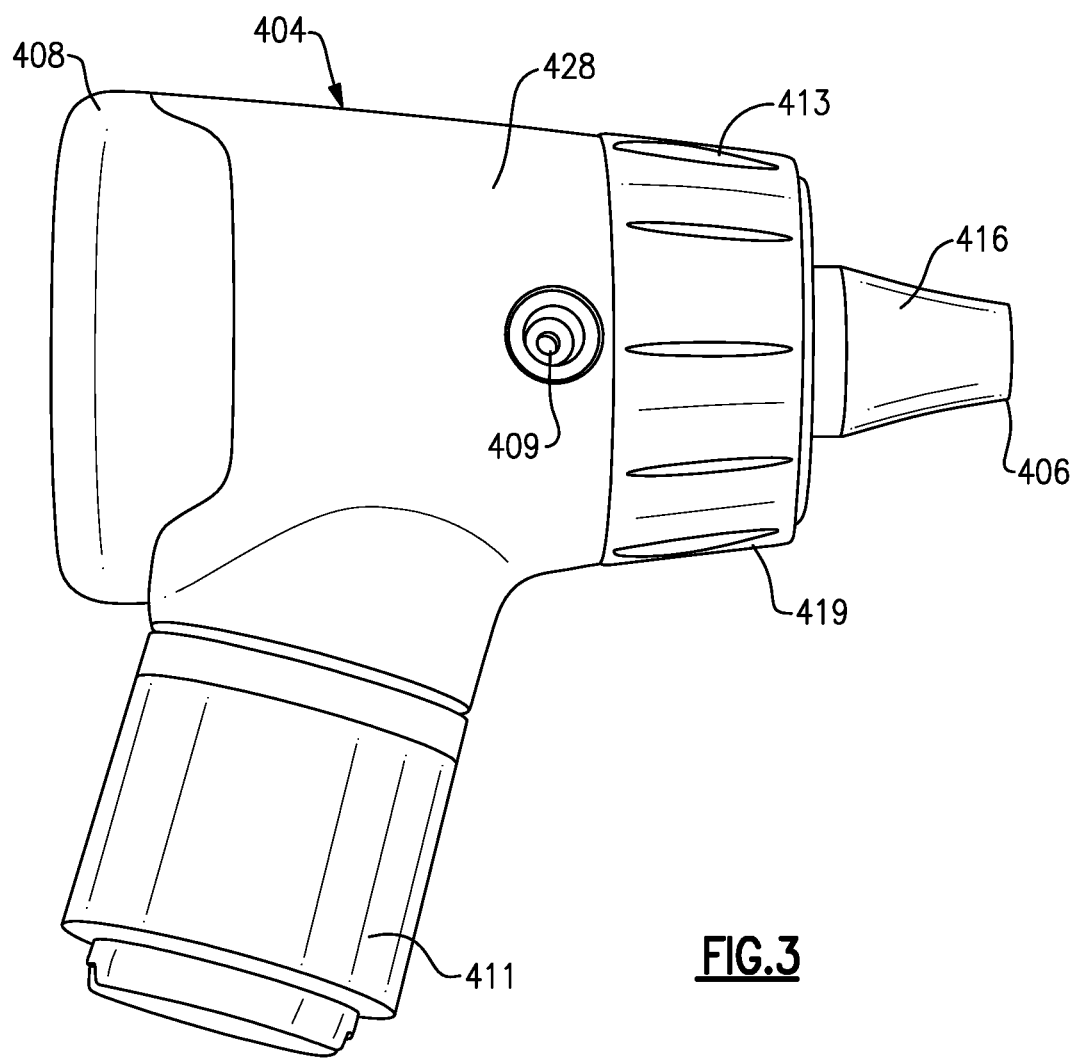
FIG. 3 is a perspective view of a medical diagnostic instrument made in accordance with an embodiment.
Figure 4A:
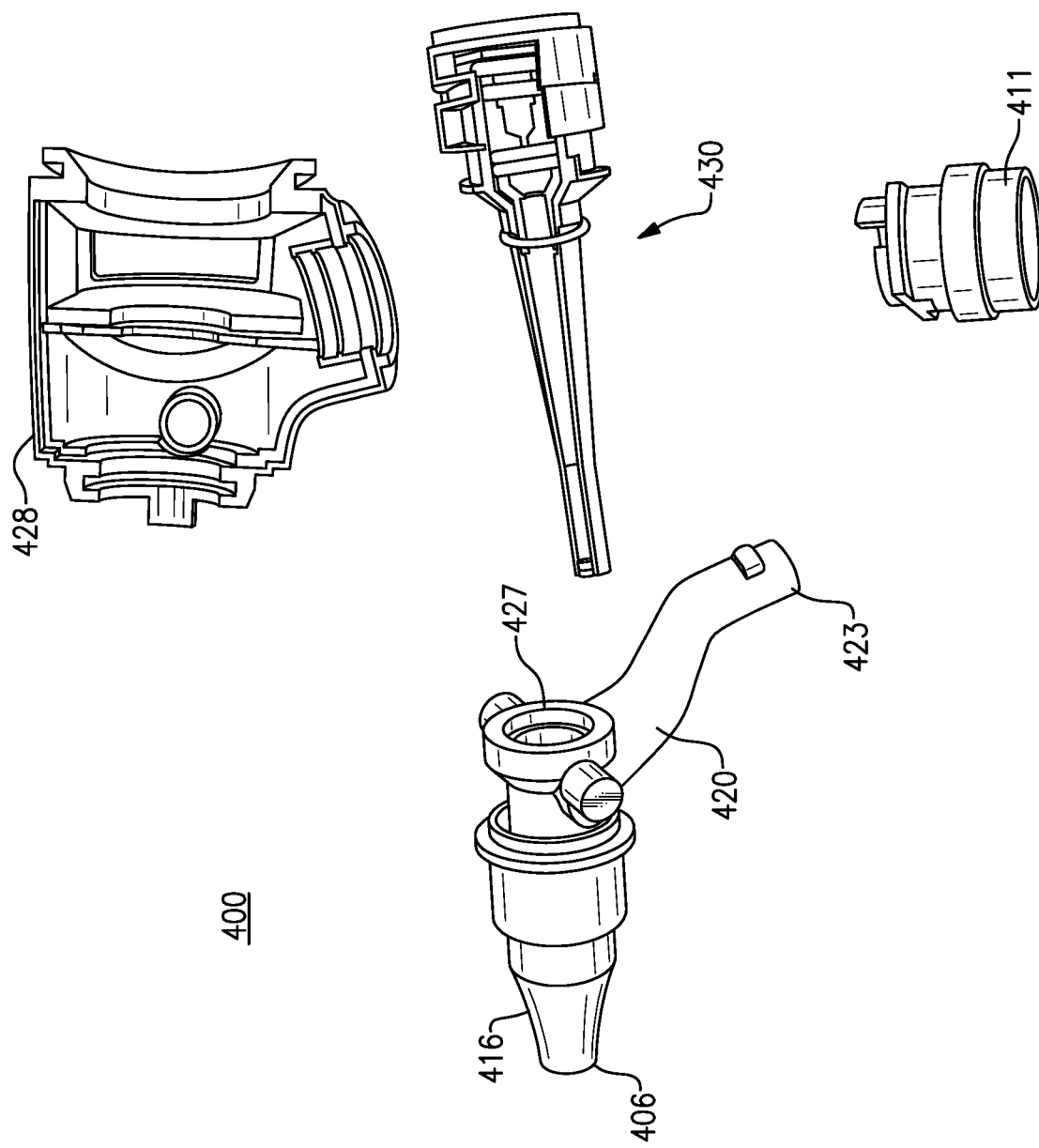
FIGS. 4(a)-4(g) are partial assembly views, shown in sequence, of the medical diagnostic instrument of FIG. 3.
Figure 4B:
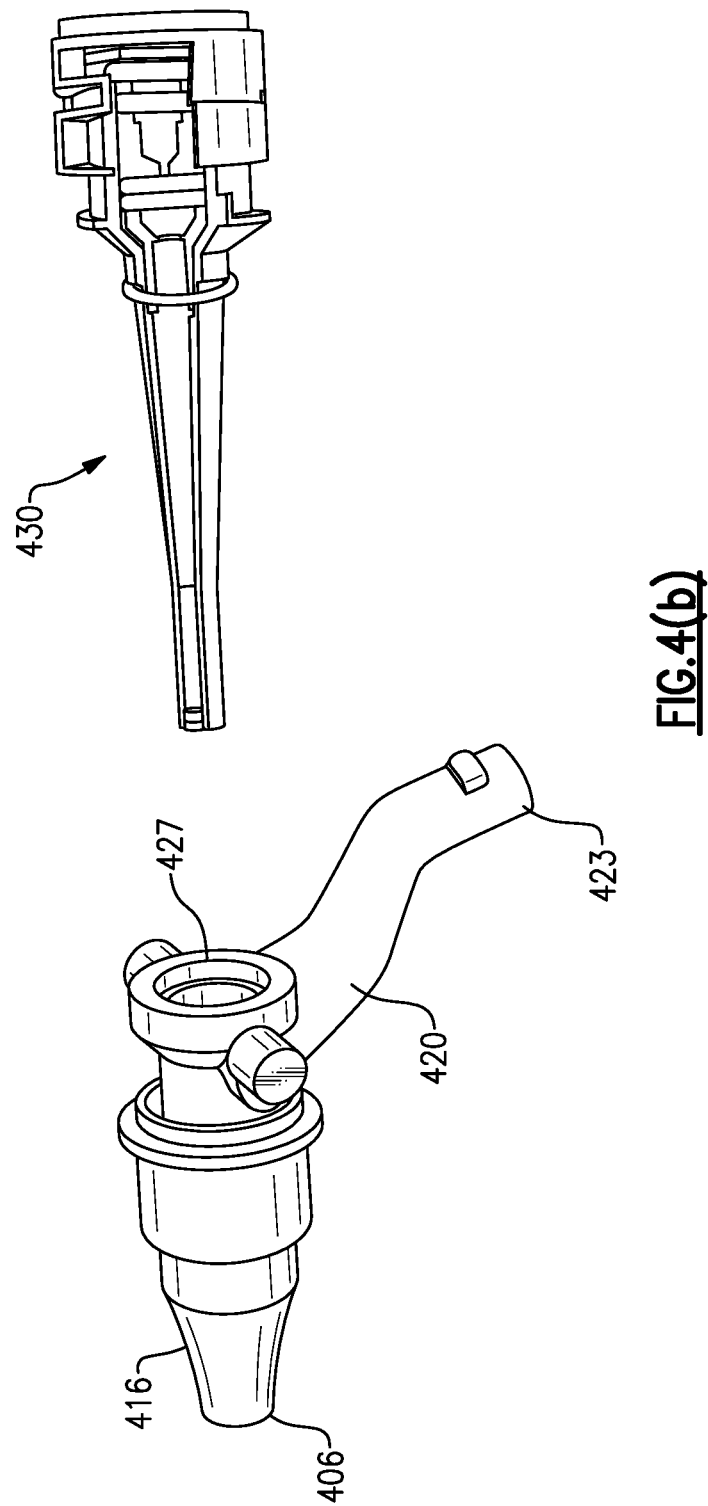
Figure 4C:
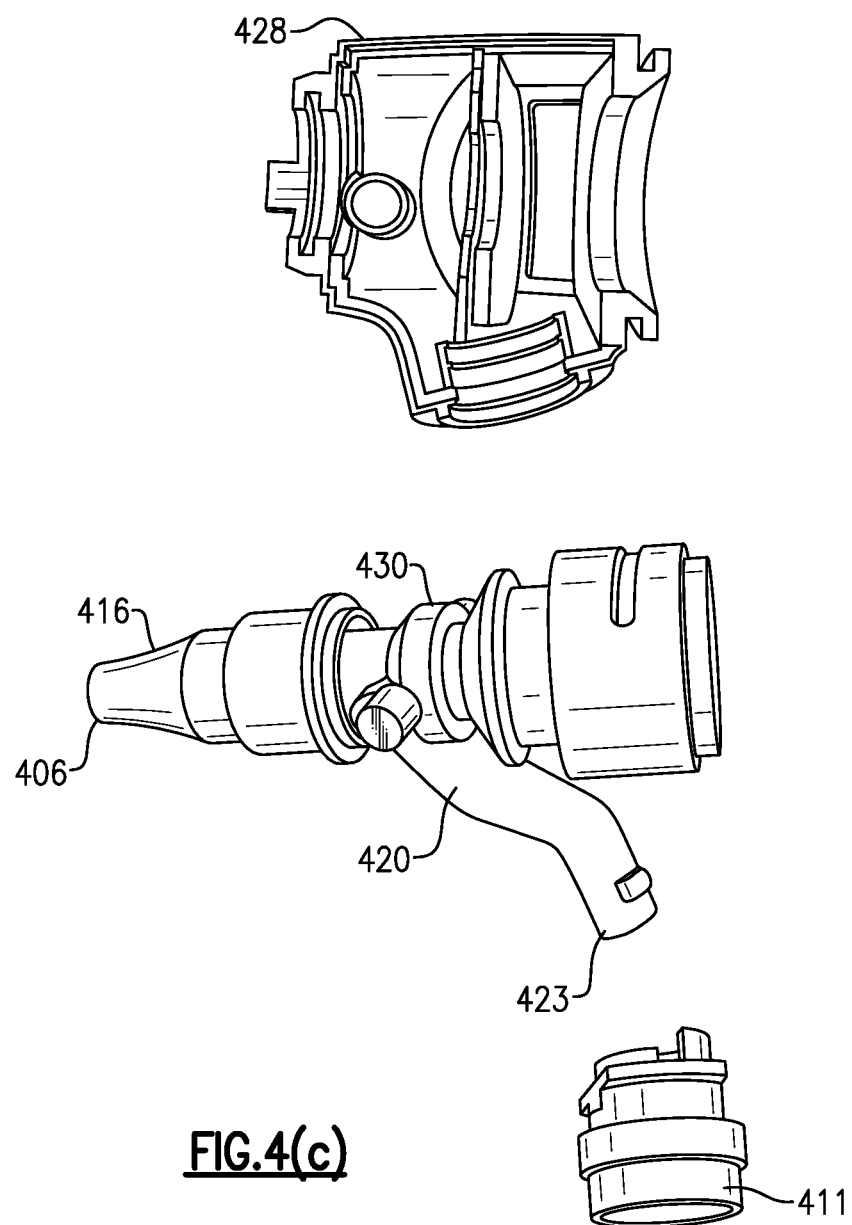
Figure 4D:
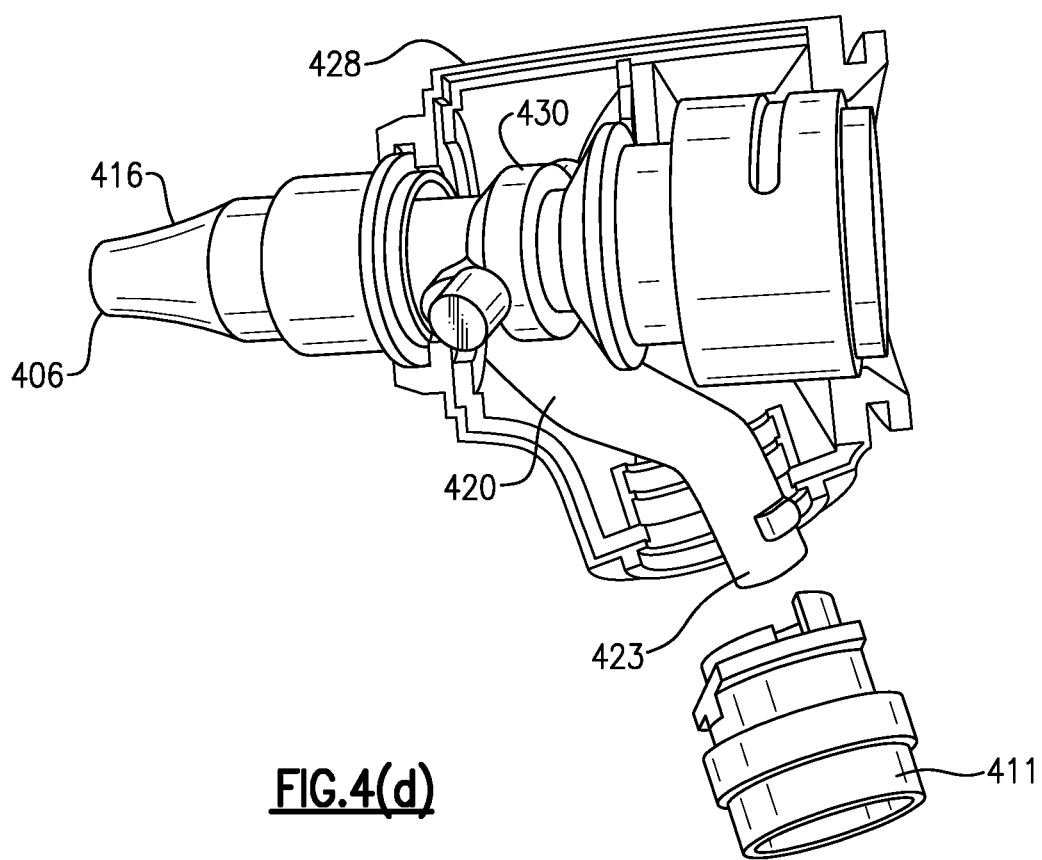
Figure 4E:
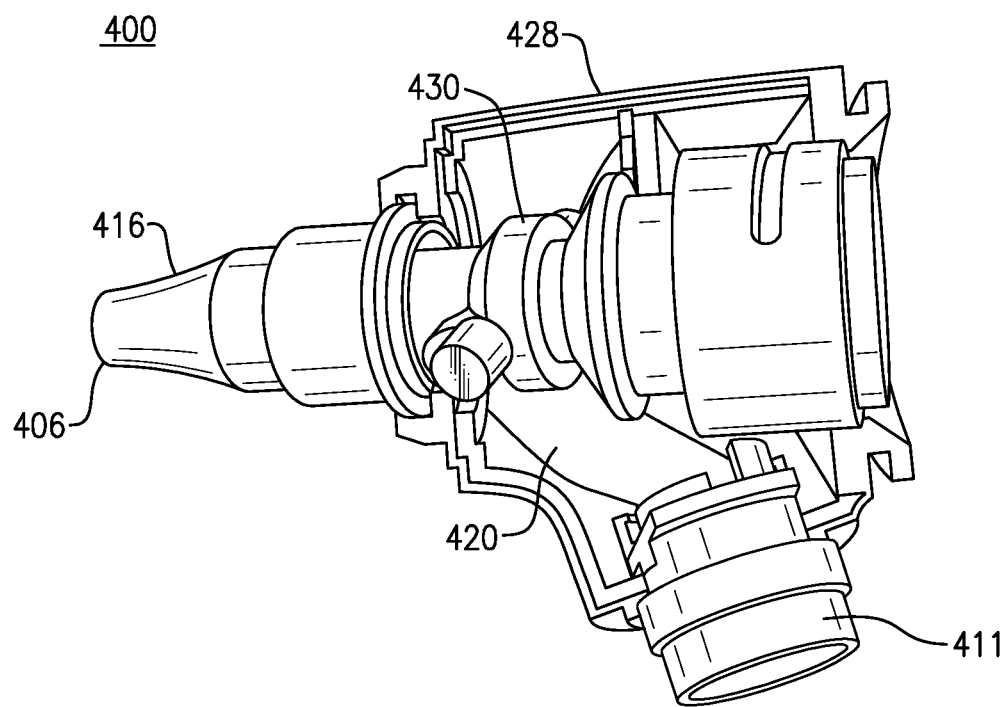
Figure 4F:
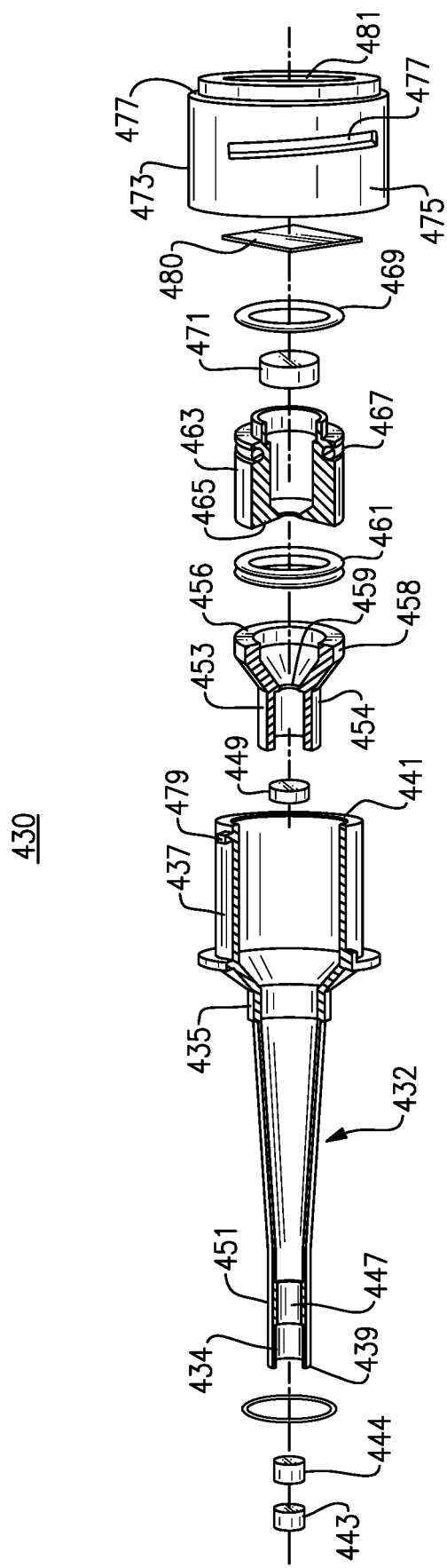
Figure 4G:
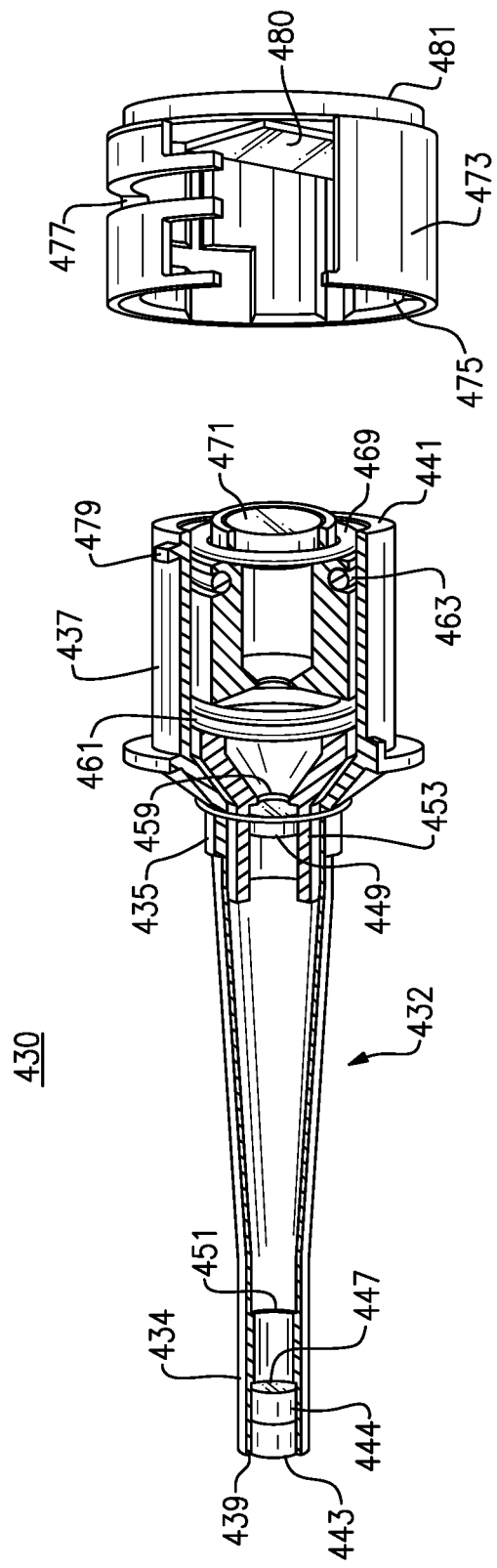

A medical diagnostic instrument made in accordance with a first exemplary embodiment is provided in FIGS. 3-4(g). More specifically, the instrument 400 is an otoscope having an instrument head 404 defined by respective distal and proximal ends 406, 408. An illumination connector 411 extends from the bottom of the instrument head 404, which is mechanically and electrically connected to the upper end of an instrument handle (not shown). The instrument head 404 includes a cover 428 having an insufflation port 409, as well as an attachment and retention mechanism 413 for releasably securing a speculum tip (not shown) in overlaying fashion onto a substantially conical distal insertion portion 416, the latter mechanism including a rotatable actuator knob 419 disposed in relation to the insertion portion 416.

Though not shown, the illuminator connector 411 is configured to engage the upper end of the instrument handle, using a bayonet-type connection and in which the instrument handle is configured to retain at least one battery (not shown), such as a rechargeable battery. A light source (not shown) such as an incandescent lamp or bulb is further provided at the upper end of the instrument handle in relation to a bundle of optical fibers. The proximal ends of the optical fiber bundle are polished and optically coupled with the light source. The optical fiber bundle extends into the instrument head 404 and encircle the interior diameter of a distal opening 406 of the conical distal insertion portion 416. The distal insertion portion 416 is shaped and configured to releasably retain an axisymmetric speculum tip, the latter being configured for insertion to a predetermined distance into the ear canal. The actuator knob 419 of the tip attachment and retention mechanism 413 is configured to engage and/or disengage with corresponding features on the speculum tip based on relative rotation between the speculum tip and the actuator knob 419. Details relating to the tip attachment and retention mechanism 413 and related aspects of the speculum tip and distal insertion portion 416 are provided, for example, in U.S. Pat. No. 7,399,275, the entire contents of which are herein incorporated by reference.

The following description details an assembly flow or process for the otoscope 400. First and as shown in FIG. 4(a), the herein described otoscope 400 is shown with various components in an exploded view including the illumination connector 411, the distal insertion portion 416, an inner former 420, an optics assembly 430, and a portion of the outer cover 428. The inner former 420 is a structural portion of the instrument 400 that includes a lower section 423 configured to receives the optical fiber bundle (not shown) extending upwardly from the light source (not shown) contained within the instrument handle (not shown) for purposes of illumination, similar to that described in regard to the instrument 100 of FIG. 1 as well as an opening 427 that is sized to receive the optics assembly 430. The tip attachment and retention mechanism 413 is not shown in these assembly views for reasons of clarity.

As shown in FIGS. 4(b) and 4(c), the optics assembly 430 is configured to be fitted within the opening 427 of the inner former 420 with the outer cover 428 being further disposed about the exterior of the optics assembly 430, as shown in FIG. 4(d), and the illumination connector 411 being secured to the bottom of the assemblage, as shown in FIG. 4(e). A cutaway version of the assembled otoscope 400 is shown in FIG. 4(e) without a portion of the outer cover 428 for purposes of clarity. As shown in FIG. 4(e) and when assembled, the proximal end of the optics assembly 430 is roughly coplanar with the proximal end of the instrument head (i.e., cover 428).

The components of the herein described optics assembly 430 are shown in an exploded view in FIG. 4(f). According to this exemplary embodiment, the optics assembly 430 is defined by a housing 432 having a three separate diametrical sections; namely, a distal section 434, an intermediate section 435, and a proximal section 437. According to this embodiment, the distal section is defined by an extended length terminating at the intermediate section 435, the latter having a larger interior diameter than the distal section 434 and the proximal section 437 having a larger diameter than that of the intermediate and distal sections 434, 435. Overall, the housing 432 is defined by a cylindrical configuration having tapered axial sections between the distal and intermediate sections 434 and 435 and between the intermediate section 435 and the proximal section 437 of the housing 432.

The housing 432 is essentially hollow and is further defined by respective distal and proximal end openings 439, 441 in which the housing 432 is further configured to support a plurality of optical components. A plano window 444 is disposed at the distal end 439 of the housing 432 in the distal section 434 with an objective lens 447 being proximally disposed adjacent a plano window 444. According to this exemplary embodiment, the objective lens 447 is made from an optical grade plastic, although alternatively, other materials that have optical quality can be substituted. Referring to FIGS. 4(f) and 4(g), a relay lens 449 is further disposed within the intermediate section 435 of the housing 432, with a field stop 451 being disposed between the relay lens 449 and the objective lens 447.

Still referring to FIGS. 4(f) and 4(g), a first spacer 453 is proximally disposed relative to the relay lens 449. The first spacer 453 is defined by a substantially cylindrical configuration having a distal portion 454 that extends into the intermediate section 435 of the housing 432, a proximal section 456 that is disposed within the proximal section 435 of the housing 432 and an intermediate portion 458 having a taper corresponding to the taper formed between the intermediate and proximal sections 435, 437 of the housing 432. The first spacer 453 is substantially hollow, other than being configured with an interior narrowed aperture 459 which is intended to block stray light, the first spacer 453 and aperture 459 being centrally aligned with an optical axis of the assembly 430. A pair of O-rings 461 are disposed between the first spacer 453 and a proximally disposed second spacer 463, wherein a field stop 465 is disposed at the distal end of the second spacer 463. When assembled, the second spacer 463 is disposed within the proximal section 437 of the housing 432 and includes a series of exterior peripheral grooves 467 at the proximal end thereof that are sized and configured to retain at least one O-ring 469. An eyepiece lens 471 is retained at the proximal end of the second spacer 463. A retaining cap 473 is configured to engage the exterior of the third section 437 of the housing 432 in which the retaining cap 473 is defined by a cylindrical configuration having an open distal end 475 as well as a set of engagement features, including annular slots 477, configured to engage corresponding exterior features 479 provided on the exterior of the proximal portion 437 of the housing 432 when the retaining cap 473 is attached thereupon and twisted or rotated in a first direction.

The retaining cap 473 is further configured to retain a plano window 480 that is sandwiched between a rear or proximal wall of the retaining cap 473 and the proximal end of the housing 432, including the eyepiece lens 471, wherein the rear wall of the retaining cap 473 further includes a proximal viewing opening 481.

As assembled, the plano windows 443, 480 at the distal and proximal ends of the housing 432 provide an effective seal relative to the interior of the optics assembly 430. Other than the relative sizes of the lenses 447, 449 and 471, each of the lenses used herein according to this exemplary embodiment are symmetric, meaning that both the distal and proximal facing sides are defined by the same curvature, which according to the present embodiment is a biconvex design. In addition, each of the lenses 447, 449, 471 according to this exemplary embodiment are made from an optical grade plastic, although any or all of the lenses could also be made from glass or other suitable material of optical quality. At the time of assembly, the engagement of the O-ring 469 as well as the O-rings 461 between the first and second spacers 453 and 469 can create a spring force when engaged by the retaining cap 473, when twisted, that enables slight focus adjustments to be made to the herein described optics assembly 430.

Figure 11:
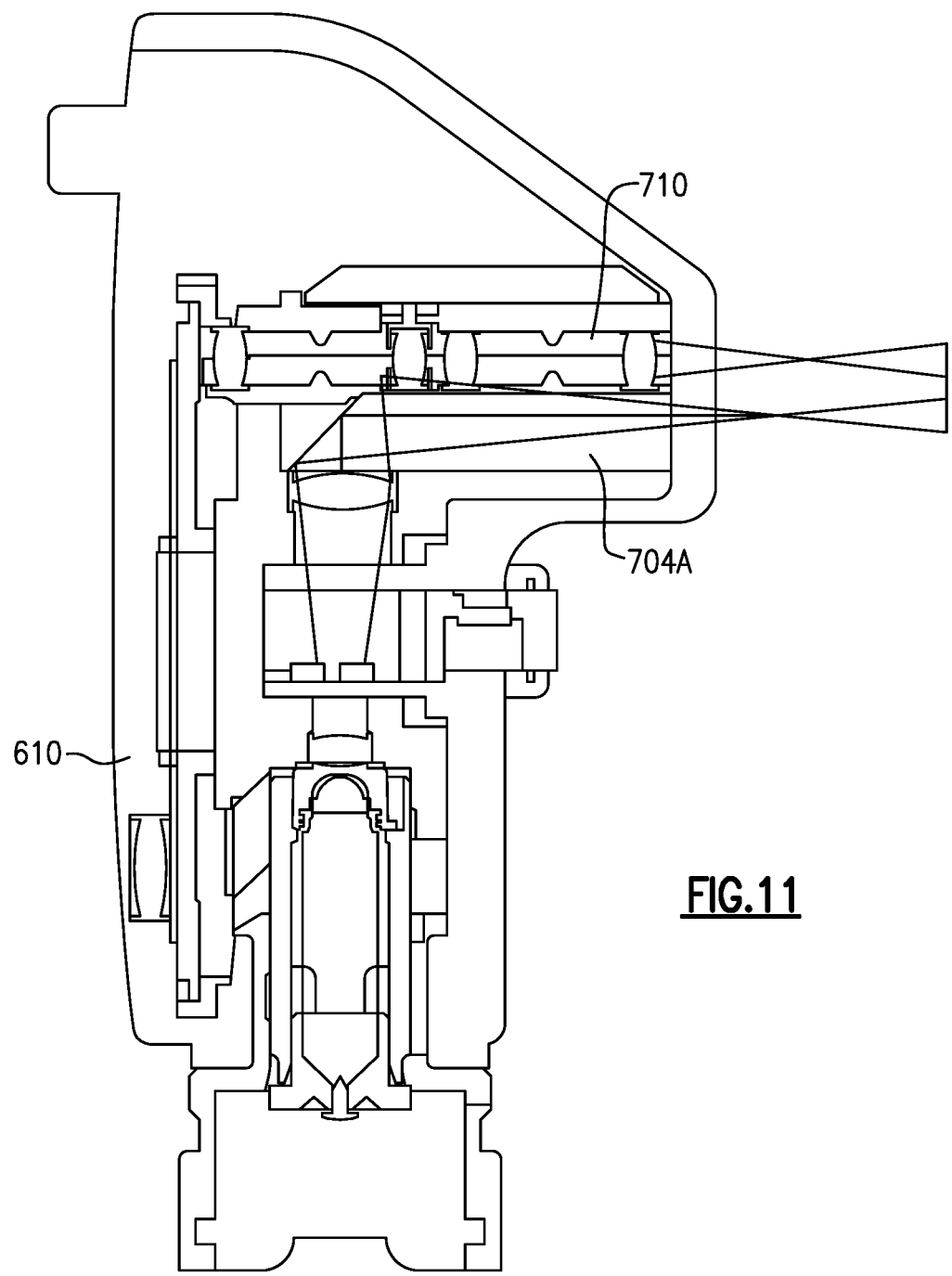
FIG. 11 is a side elevational view, shown in section, of a medical diagnostic instrument in accordance with yet another embodiment.

When assembled, the distal end of the optics assembly 430 extends into the interior of the conical insertion portion 416 and is substantially aligned with the distal opening 406 thereof. With reference to the optical trace diagram provided at FIG. 11, illumination from a contained light source in the instrument handle (not shown) can be directed through the distal opening 406 of the instrument head 404 in a manner that is known and in which an enhanced (larger) field of view as compared to prior otoscopes, such as previously described according to FIG. 1, is produced. More specifically, the herein described optics assembly 430 creates an entrance pupil 483 that is distal to the distal opening 406 of the otoscope 400 in which the contained objective lens 447, relay lens 449 and eyepiece lens 471 create a upright image of the target of interest through imaging plane 482. The field stop 451 is provided to reduce the effects of glare while the field stop 465 narrows the light relative to the eyepiece lens 471, creating a borescopic optical train that effectively shifts the location of the caregiver's pupil to the entrance pupil 483, thereby creating an expansive field of view.

Figure 5:
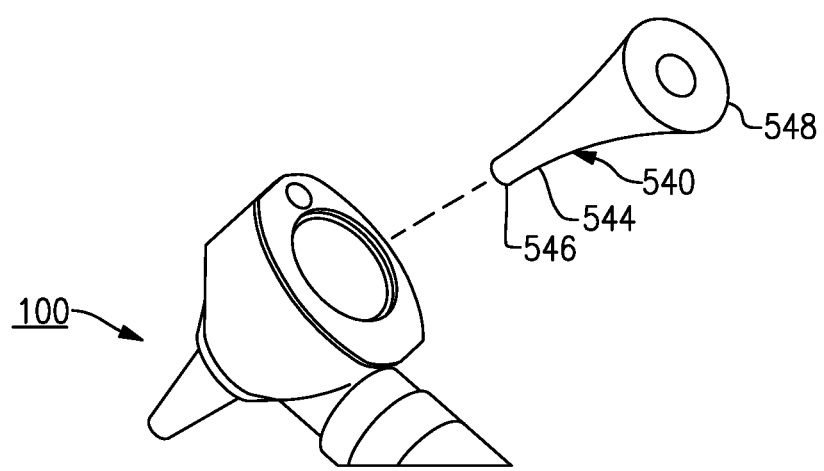
FIG. 5 is a simplified perspective view of a modular version of an optical system for releasable attachment to a medical diagnostic instrument and in accordance with another embodiment.
Figure 6:
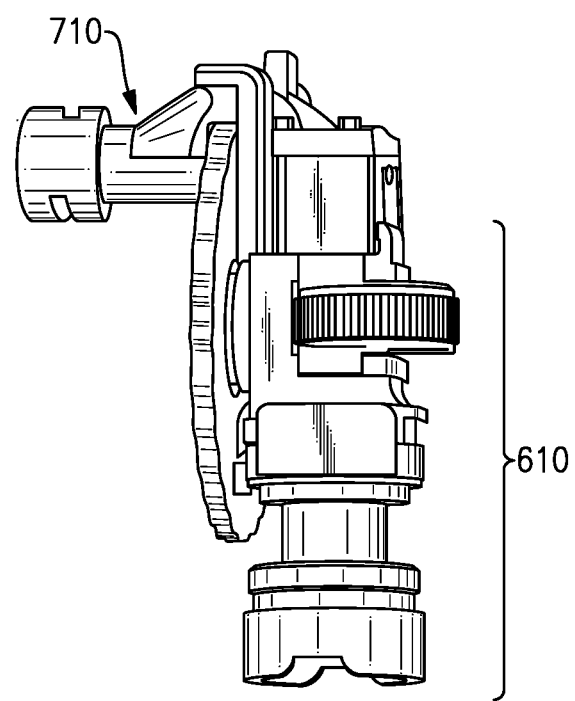
FIG. 6 is a partially assembled side elevational view of a medical diagnostic instrument made in accordance with another embodiment.

Referring to FIG. 5 and shown schematically, an alternative instrument version can be contemplated in which an optical module 540, similar to the herein described optical assembly 430, can be releasably disposed within the interior of an otoscope, such as the prior art version 100, FIG. 1, in lieu of providing an optical assembly that is already integrated within the instrument. According to this version, the module 540 can have a similar configuration to that of the optics assembly of the previously described instrument, the module 540 being defined by a tapering housing 544 that includes a distal end opening 546 and a opposing proximal end opening 548 that are axially aligned along a defined optical axis with the distal and proximal ends of the instrument housing. As in the preceding version, the contained optics produce a virtual pupil equivalent to that of the caregiver's eye which is created distally relative to the distal end of the instrument with the light being directed through a contained relay lens system to the caregiver's eye.

At least one additional pair of relay lenses could be provided in tandem along the herein described optical axis of the instrument, depending on the application/use of the instrument.

A medical diagnostic instrument made in accordance with another exemplary embodiment is herein described with reference to FIGS. 6-8(f). The instrument 600 described in accordance with this embodiment is an ophthalmoscope, partially shown without a cover and instrument handle in FIG. 6, which is configured to function similarly to that previously described with reference to FIG. 2. The herein described version includes an illumination assembly 610, having a plurality of components, as well as a viewing or optical assembly 710.

Figure 7A:
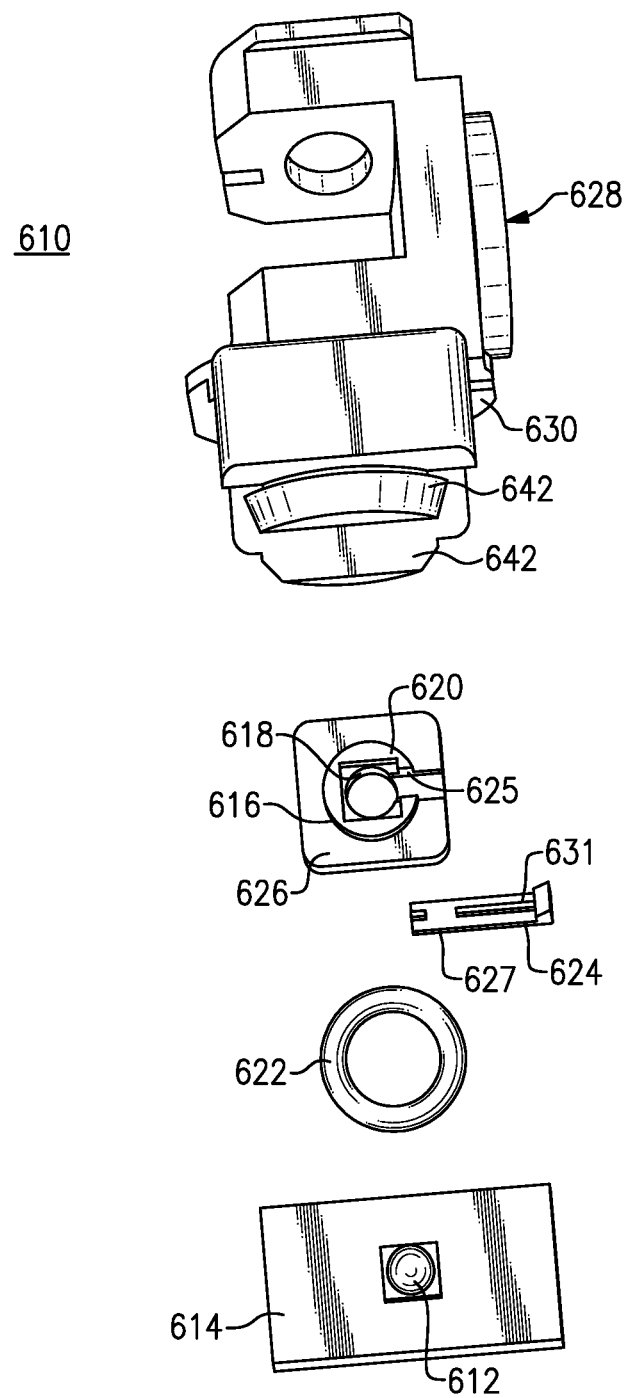
Figure 7B:
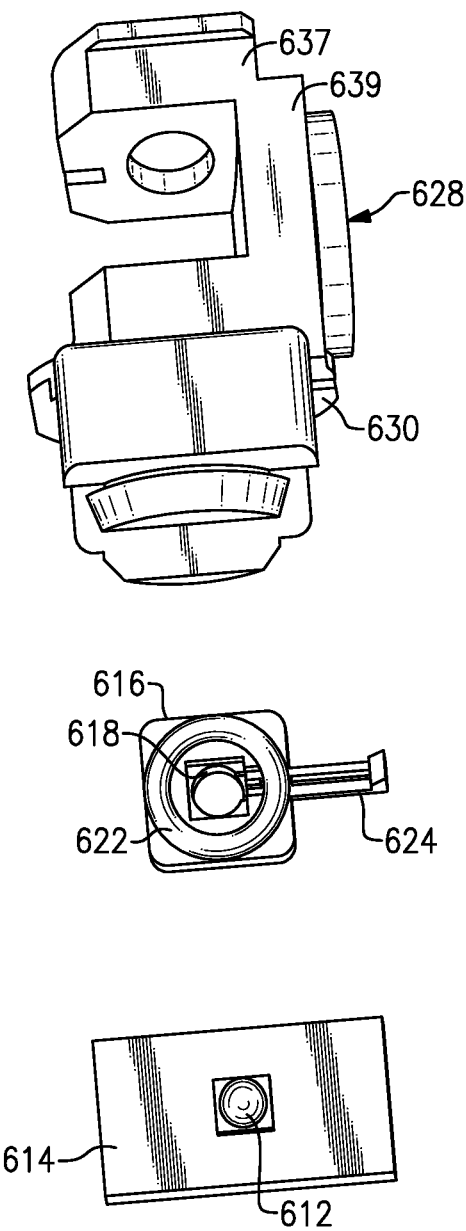

First referring to FIGS. 7(a)-7(k), the assembly flow of an illumination assembly 610 is herein described. As discussed herein, the major components of the illumination assembly 610 can be constructed using a set of interlocking components, facilitating the process of manufacture. At an initial point of assembly and referring to FIG. 7(a), a first series of components are assembled including an LED 612, such as a white LED, that is disposed onto a upper facing surface of a circuit board 614. A spacer 616 used in the subassembly includes a defined through aperture 618, as well as a lower flange 620 that is sized to retain an O-ring 622. A curved light pipe 624, made from a light conducting plastic, can be assembled with a portion 627 of light pipe being retained within a slot 625 formed in the bottom surface 626 of the spacer 616 and in which the light pipe 624 includes an external notch 631 that enables the 0O-ring 622 to secure the light pipe 624 in a predetermined position. Referring to FIGS. 7(c) and 7(d), the spacer 616 can be fitted within a defined recess 629, FIG. 7(c), that is formed in a lower portion 630 of an assembly support member 628 relative to an aperture 634 that retains a lens element 636, which according to this embodiment is an objective lens. A slot 638 is provided in the lower portion 630 of the assembly support member 628 adjacent the recess 629 that permits the retained light pipe 624 to extend outwardly from the assembly 610, as shown in FIG. 7(d).

In terms of assembly flow and prior to assembling the spacer 616, the objective lens 636 is placed into the aperture 634 defined in the lower portion 630 of the assembly support member 628. The assembly support member 628 according to this embodiment includes the lower portion 630, as well as an upper portion 637 and an intermediate portion 639. The lower portion 630 of the assembly support member 628 is recessed with a bottom surface having the recess 629 being disposed between a pair of projecting leg portions 642 that are configured and spaced in order to receive an illumination connector 650 as well as the LED 612 and circuit board 614.

Figure 7E:
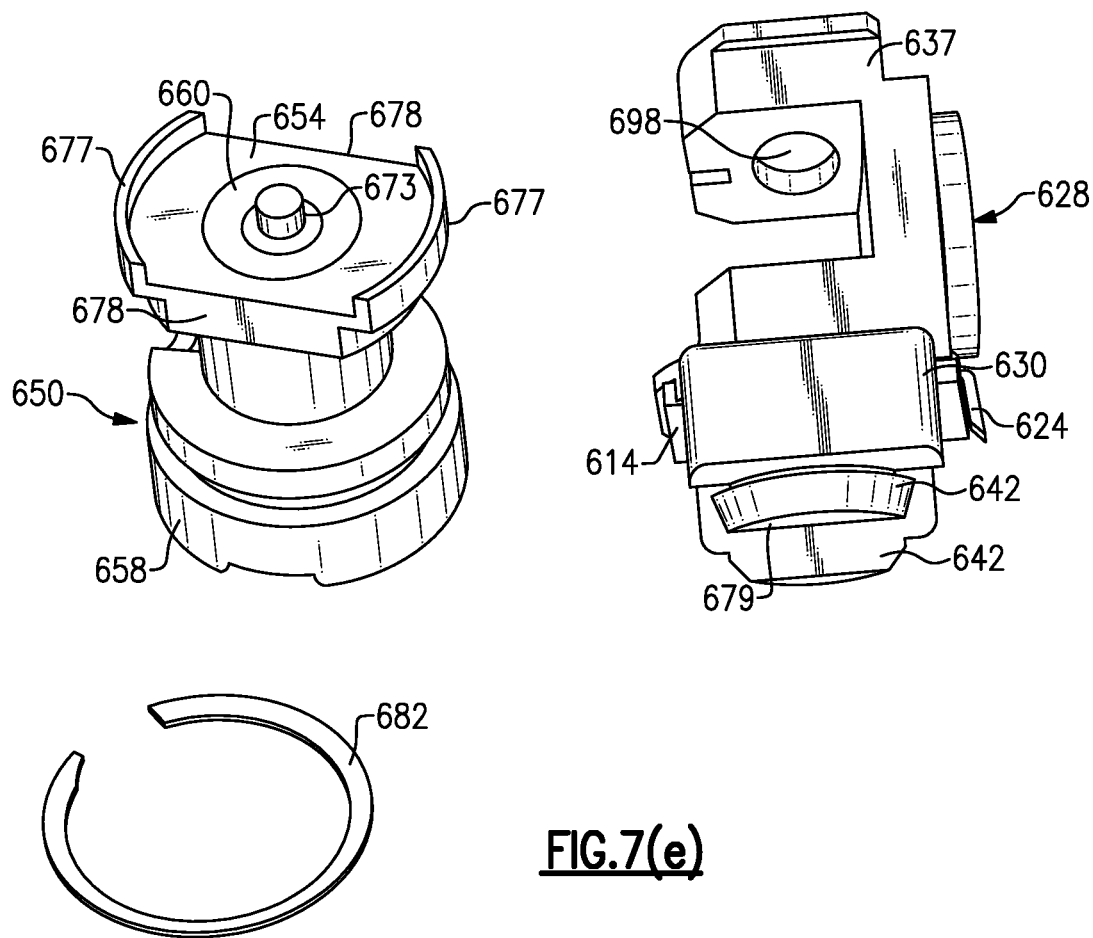
Figure 7F:
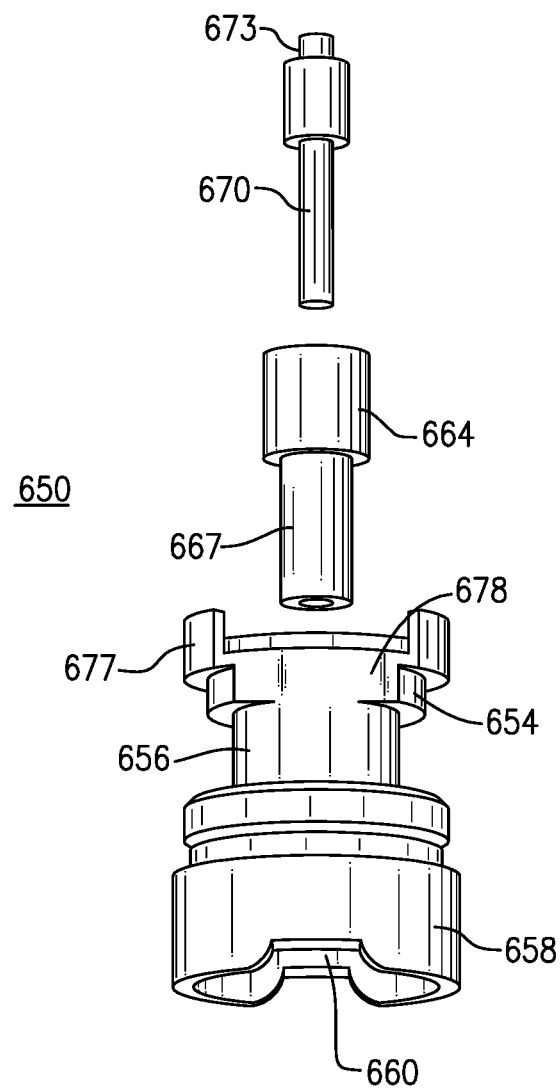
Figure 7G:
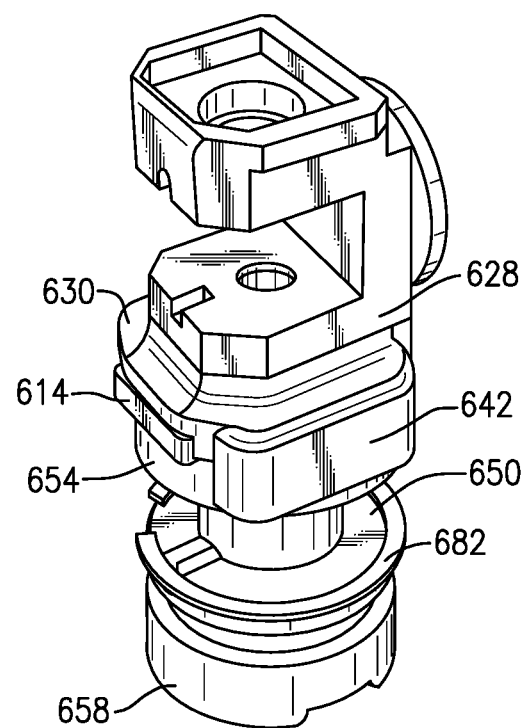
Figure 7H:
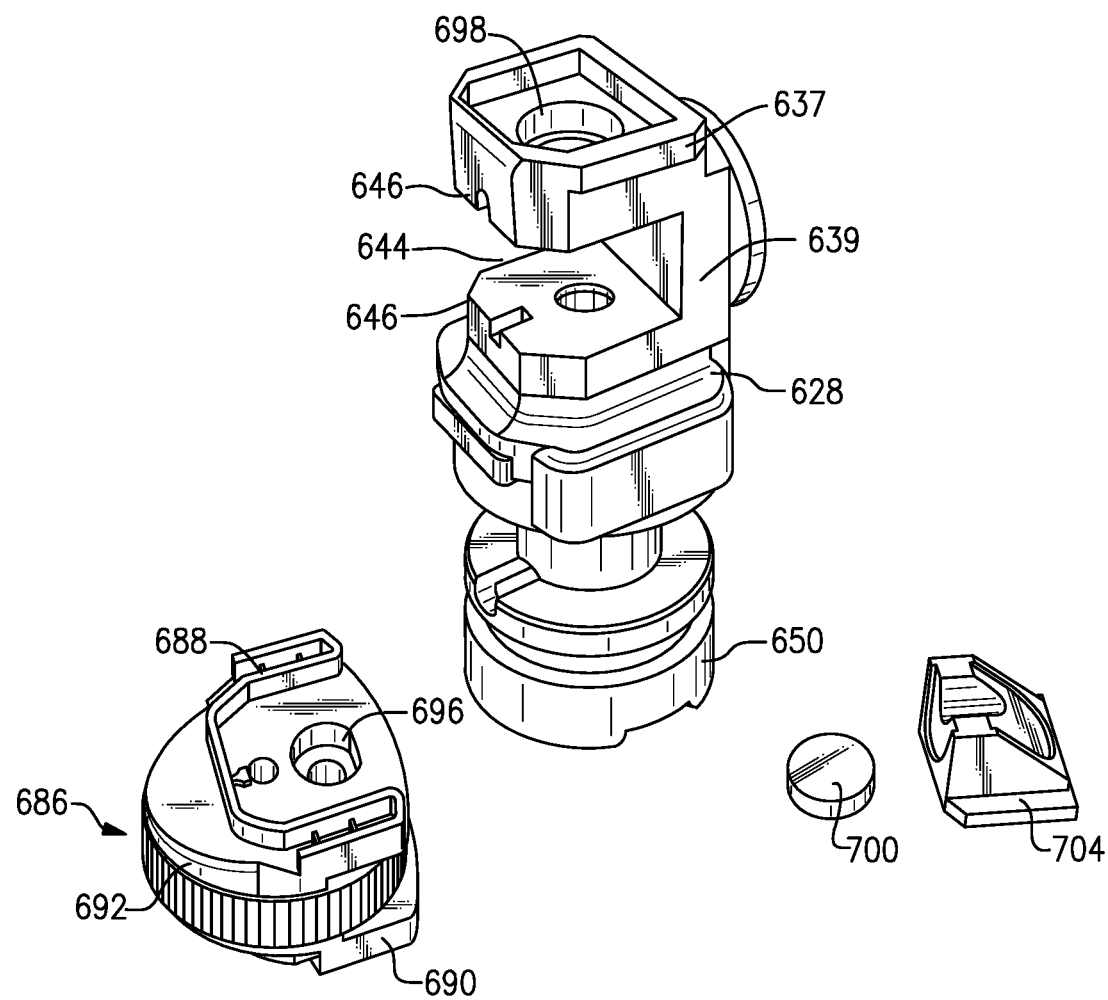
Figure 7I:
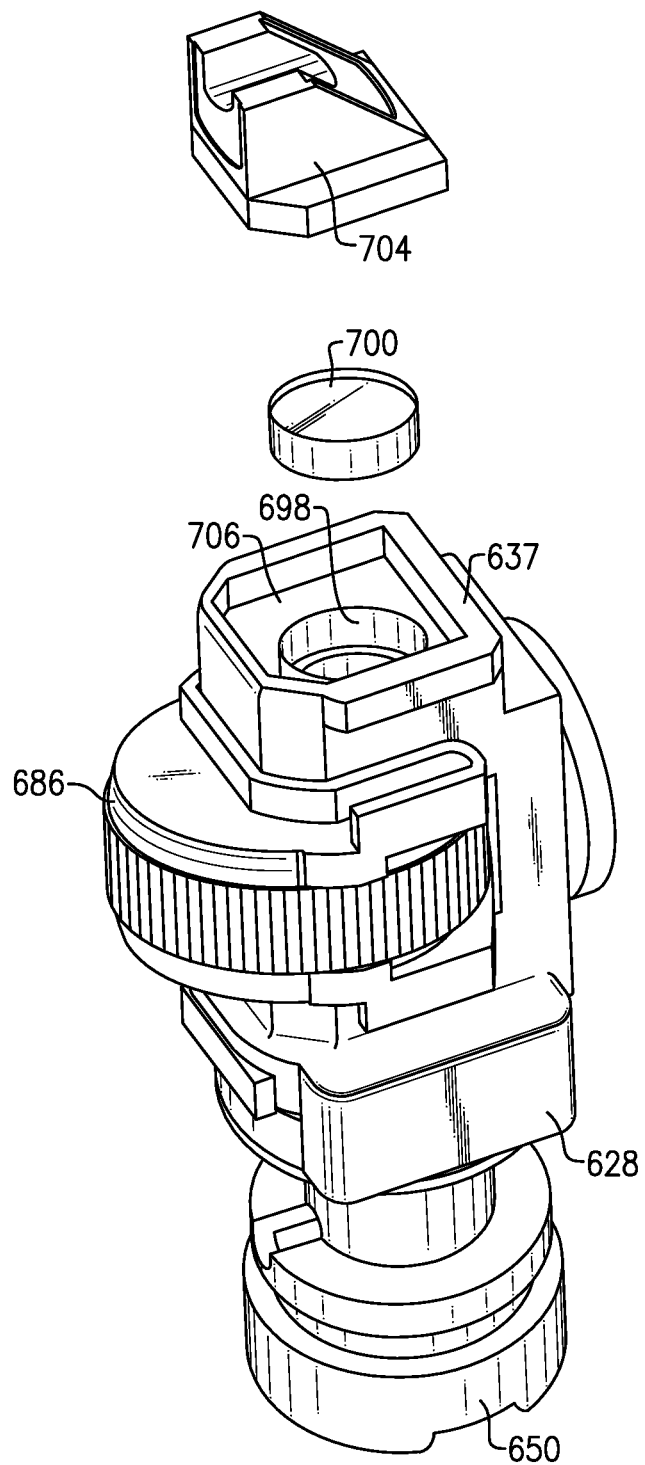
Figure 7J:
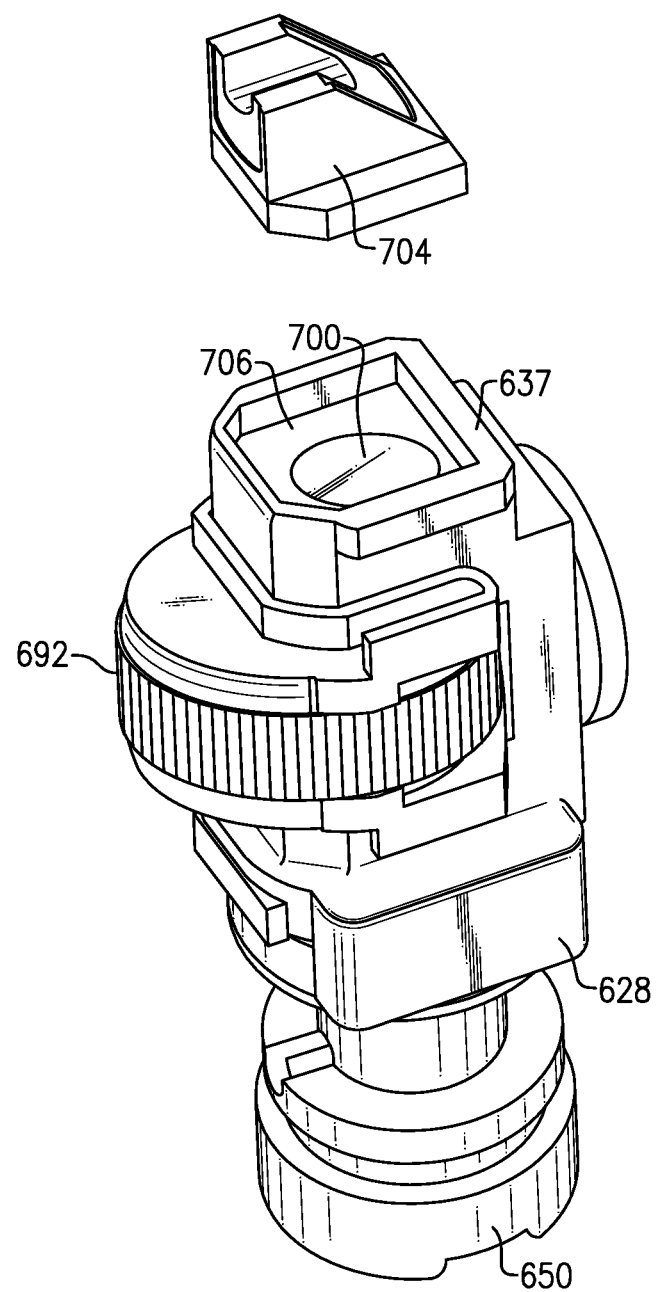
Figure 7K:
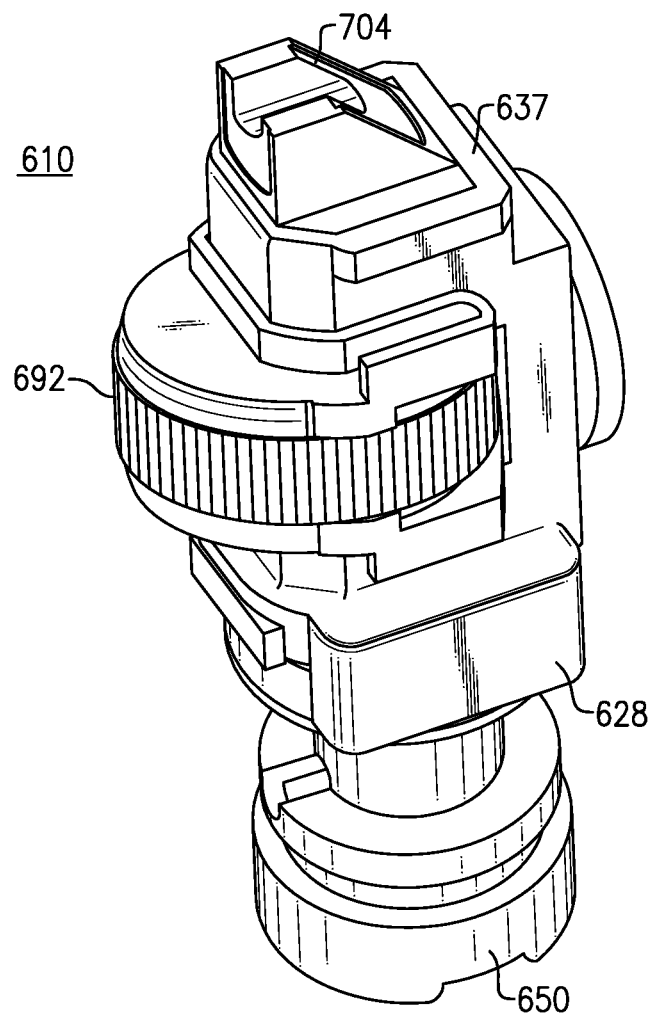

Referring to FIG. 7(e), the assembly support member 628 and more specifically the lower portion 630 thereof, is configured to receive the illuminator connector 650, shown partially exploded in FIG. 7(f). The illuminator connector 650 according to this exemplary embodiment is defined by an upper portion 654, a necked intermediate section 656, and a lower section 658, the latter section being defined with a bayonet-type connector. The connector 650 is defined by a through axial center opening 660 defined by a first diameter extending into the intermediate necked portion 656 and a narrower diameter extending into the lower portion 658, which is essentially hollow. A hollow insulator 664 is installed within the center axial opening 660 of the upper portion 654 of the illuminator connector 650 with a lower portion 667 of the insulator 664 being sized to extend partially into the lower portion 658. A center conductor 670 made from an electrically conductive material is similarly fitted within the confines of the hollow insulator 664. When installed, and as shown in the assembled condition of FIG. 7(e), an axial contacting end 673 of the center connector 670 extends outwardly from the insulator 664, with the end of the insulator 664 being substantially flush with the top surface of the illuminator connector 650, as shown in FIG. 7(*e*).

Referring to FIGS. 7(*e*), (f) and (g), the upper portion 654 of the illuminator connector 650 is shaped and configured to releasably engage the lower portion 630 of the assembly support member 628, as shown in FIG. 7(*g*) in an interlocking manner. More specifically and according to this exemplary embodiment, the upper portion 654 is defined by a pair of diametrically opposed curved portions 677 and a pair of flats 678 that are spaced to fit between the extending leg portions 642 of the lower portion 630. The curved portions 677 extend above the plane of the top surface of the illuminator connector 650 to provide ample spacing for the LED 612 and circuit board 614 which is sandwiched therebetween such that the axial contacting end 673 of the center connector 670 can be brought into contact with the circuit board 614. When assembled according to this configuration, the LED 612 and circuit board 614 are retained between the spacer 616 and more specifically, the O-ring 622 and the center conductor 670 of the illumination connector 650 with the curved portions 677 of the illuminator connector 650 being aligned with corresponding curved portions 679 formed at the bottom of the lower portion 630 of the assembly support member 628. A conductive spring clip 682 can be used to secure the assembly support member 628 with the illuminator connector 650 by placement of same over the aligned curved portions 677, following assembly in the position shown in FIG. 7(*g*).

Referring to FIG. 7(*h*), and following attachment of the assembly support member 628 to the illumination connector 650, a reticle wheel assembly 686 can be attached to the intermediate portion of the assembly support member 628. According to this embodiment, the reticle wheel assembly 686 includes an upper engagement portion 688, a lower engagement portion 690 and an aperture wheel 692 that is supported for rotation and disposed between the upper and lower engagement portions 688, 690. The reticle wheel assembly 686 is fitted within a defined recess 644 formed in the intermediate section 639 of the assembly support member 628. More specifically, respective upper and lower surfaces defining the recess 644 each include engagement rails 646 that are configured to engage sidewalls of the upper and lower engagement portions 688, 690 of the reticle wheel assembly 686 with the reticle wheel assembly 686 being sized to fit in an interlocking manner with the assembly support member 628. When assembled, a through aperture 696, including a reticle, is aligned with the LED 612, FIG. 4(*a*), and the lens element along an illumination axis of the assembly 610, as well as a through aperture 698 in the upper section 637 of the assembly support member 628, as shown in FIG. 7(*i*).

As shown in FIGS. 7(*i*) and 7(*j*), a reticle lens 700 is then placed into the through aperture 698. As shown in FIG. 7(*k*), a prismatic member 704 is then attached to the upper portion 637 of the herein described assembly member 628 and more specifically within a receiving cavity 706 that is formed at the top of the upper portion 637 of the assembly support member 628 and in alignment with the through aperture 698. The prismatic member 704 according to this embodiment includes an angled reflective surface 707. Alternatively, a mirror could be disposed to provide similar functionality. The design of the prismatic member can be suitably varied, such as shown by prismatic member 704A in FIG. 11.

As discussed, each of the components of the herein described illumination assembly 610 can be assembled according to this embodiment in an interlocking fashion without requiring fasteners such as screws, bolts or rivets. That is, each of the components of the foregoing assembly 610 can be built onto one another in a sequential fashion, such as described with reference to FIGS. 7(*a*)-7(*k*). The components can be made, for example, from a durable plastic.

Figure 8D:
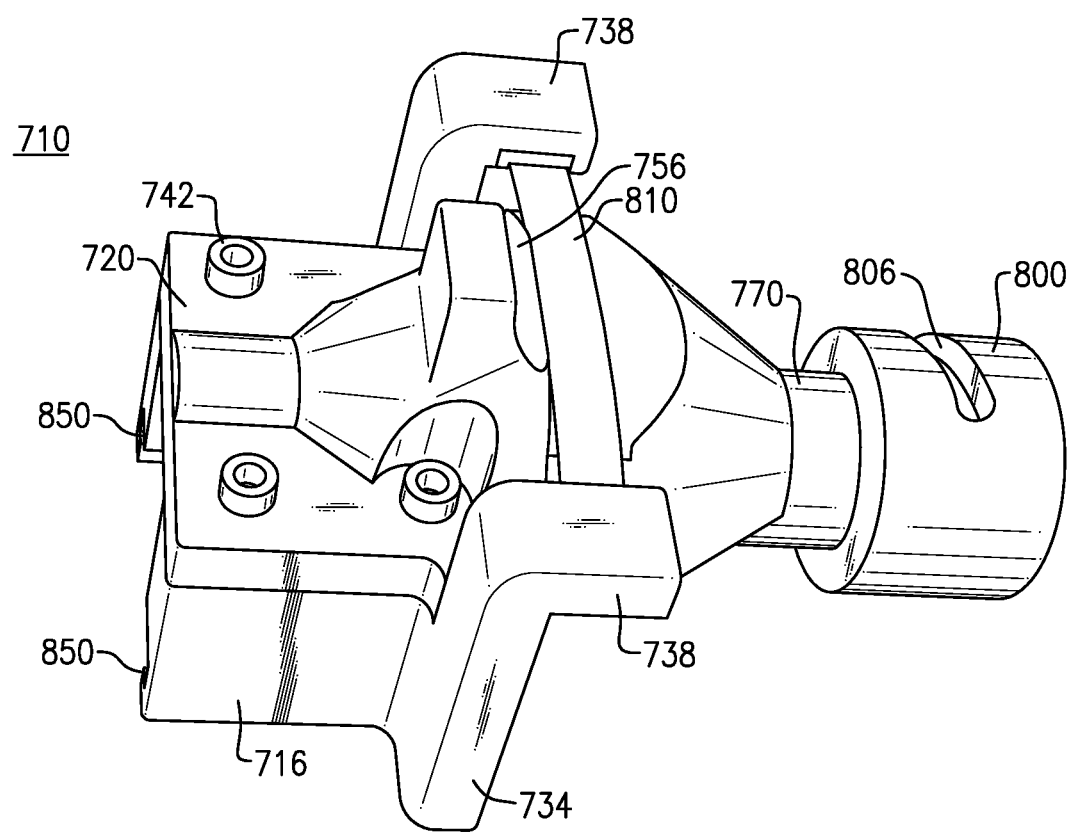

Referring to FIG. 8(*a*), an optical assembly 710 in accordance with an exemplary embodiment is disposed in relation to the herein described illumination assembly 610 prior to assembly therewith. Additional details regarding the optical assembly 710 are herein discussed with reference to FIGS. 8(*b*) and 8(*c*) in which the herein described assembly includes a housing 712 made up of an lower or bottom section 716 and an upper or top section 720. The lower section 716 is defined a top surface 724 having a semicircular groove 728 defined therein in which a first lens 732 is provided at one end of the groove 728 and a second lens 736 is defined at the opposing end of the groove 728. A pair of ears 730 extend upwardly from opposing sides of the lower section 716 relative to the second lens 736, the ears 730 including a vertical portion 734 and a transverse portion 738 extending from the top of the vertical portion 734 in substantially the same direction as the defined groove 728, but outwardly relative to the top surface 724. A plurality of posts 742 extend upwardly from the top surface 724 on opposing sides of the semicircular groove 728.

The upper section 720 of the housing 712 according to this embodiment includes a first portion 750 that is sized to cover the lower section 716, the interior surface (not shown) of this section 720 including a semicircular groove (not shown) that is aligned with the groove 728 provided on the lower section 716 and forming an optical tube with respect to the first and second lenses 732, 736. The first portion 750 is sized to be fitted between the ears 730 of the lower section 716 wherein the spaced ears 730 are sized to extend above the upper section 720 of the housing 712. A second adjacent portion 754 of the top section 720 includes a raised surface 756 that, when assembled, is substantially parallel to the top surface 724 of the lower section 716 but directly beneath and between the transverse ear portions 738, this surface 756 including a center slot or opening 760 that is sized to receive a detent 764.

A third adjoining section 766 of the housing 712 is defined by a tubular section 770 that is aligned with the semicircular groove of the first section 750. A plurality of components are disposed within the tubular section 770, which combines to form an optical system with the two lens elements 732, 736 provided in the semicircular groove 728 formed in the top surface 724 of the lower section 716. It will be understood, however, that this two-part design is exemplary and that other variations and modifications are possible.

Still referring to FIG. 8 (*b*) and (*c*), the components disposed within the tubular section 770 of the housing include a relay lens 776 that is positioned within the distal end of a lens carrier 780 having a through aperture. The lens carrier 780 is essentially hollow and for convenience can be built as a two-part assembly to enable assembly of the relay lens 776. The lens carrier 780 is defined by a substantially cylindrical section having a first diameter that is sized to support the relay lens 776 and a second diameter that is retained against a shoulder formed in the tube. An O-ring 784 is disposed between the lens carrier 780 and a spacer 790, the spacer 790 having a field stop 794 at its distal end. An eyepiece lens 798 is disposed in engagement with the proximal end of the spacer 790. Each of the lenses 776, 798 according to this configuration are symmetrical; that is, each lens 776, 798 includes identically curved (convex) distal and proximal surfaces. Additionally and according to at least one version, each of the peripheral edges of the lenses 776, 798 can be raised to prevent damage, such as scratching to the optical surfaces.

A retaining cap 800 engageable with the proximal end of the tubular section 770, the retaining cap 800 includes an open distal end 802 and engagement features, such as annular slots 806, as well as a proximal viewing opening. A plano window 804 is disposed between the eyepiece lens 798 and the rear wall of the retaining cap 800 wherein the retaining cap 800 can be twisted in order to apply a compressive force against the resilient O-rings 784 to effect minor focus adjustments at the factory level, for example, to compensate for manufacturing tolerances.

A thin sheet 810 of copper or other flexible metal can be positioned such that each end of the sheet 810 is secured beneath the extending ear portions 738 and spans across the raised surface 756 of the second section 754. As discussed herein, this portion of the assembly is used in connection with diopter wheel 840.

According to this version, the upper portion 720 of the housing 712 includes a plurality of holes 744 that can be aligned with the posts 742 of the lower portion 716 to enable the housing 712 to be secured.

Upon assembly, the optical assembly 710 can be attached to the illumination assembly 610 in which the lower portion 716 is includes a pair of spaced rail sections 850 that can be engaged with the upper portion sidewalls 698, FIG. 8(a), of the assembly support member 628.

Figure 8E:
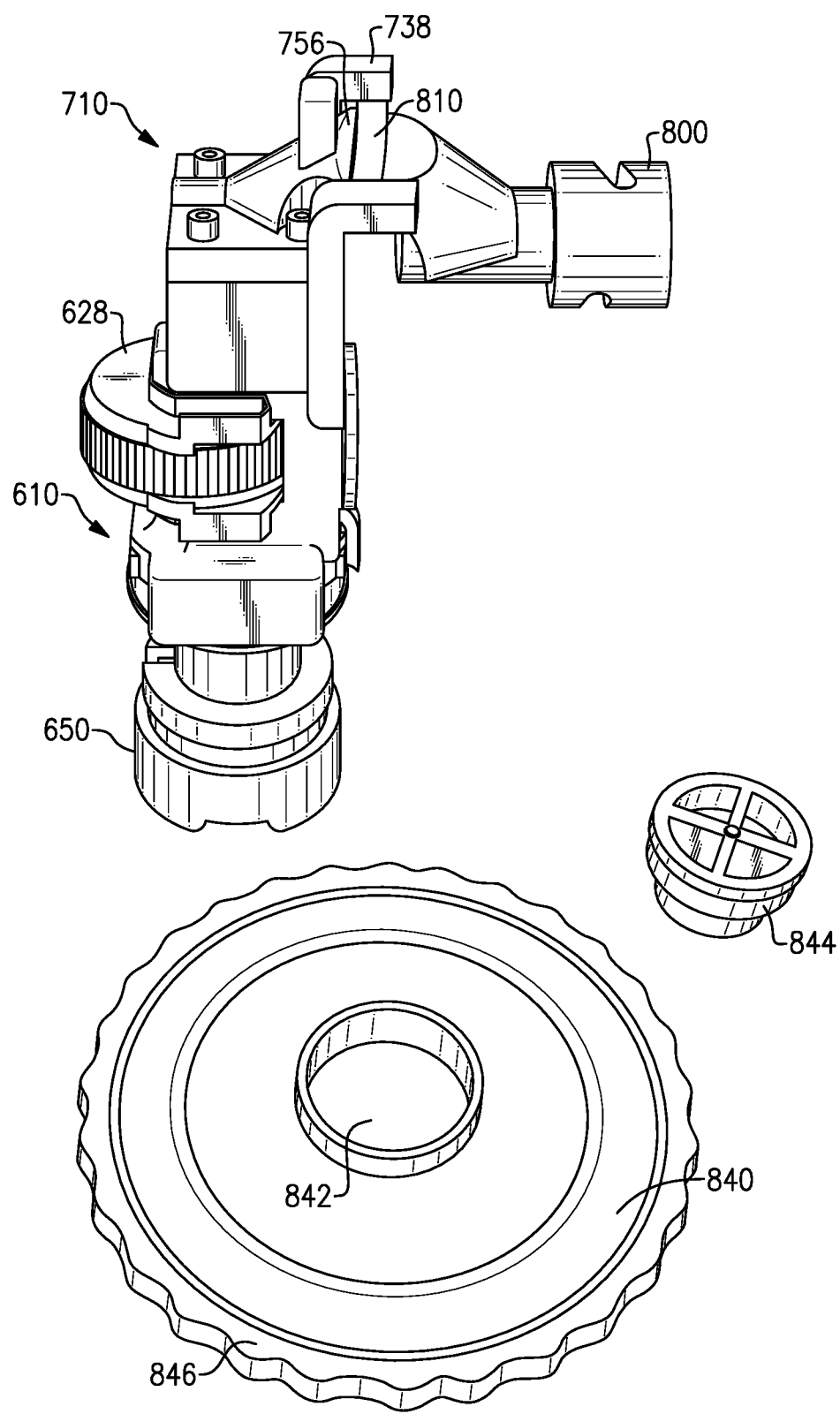
Figure 8F:
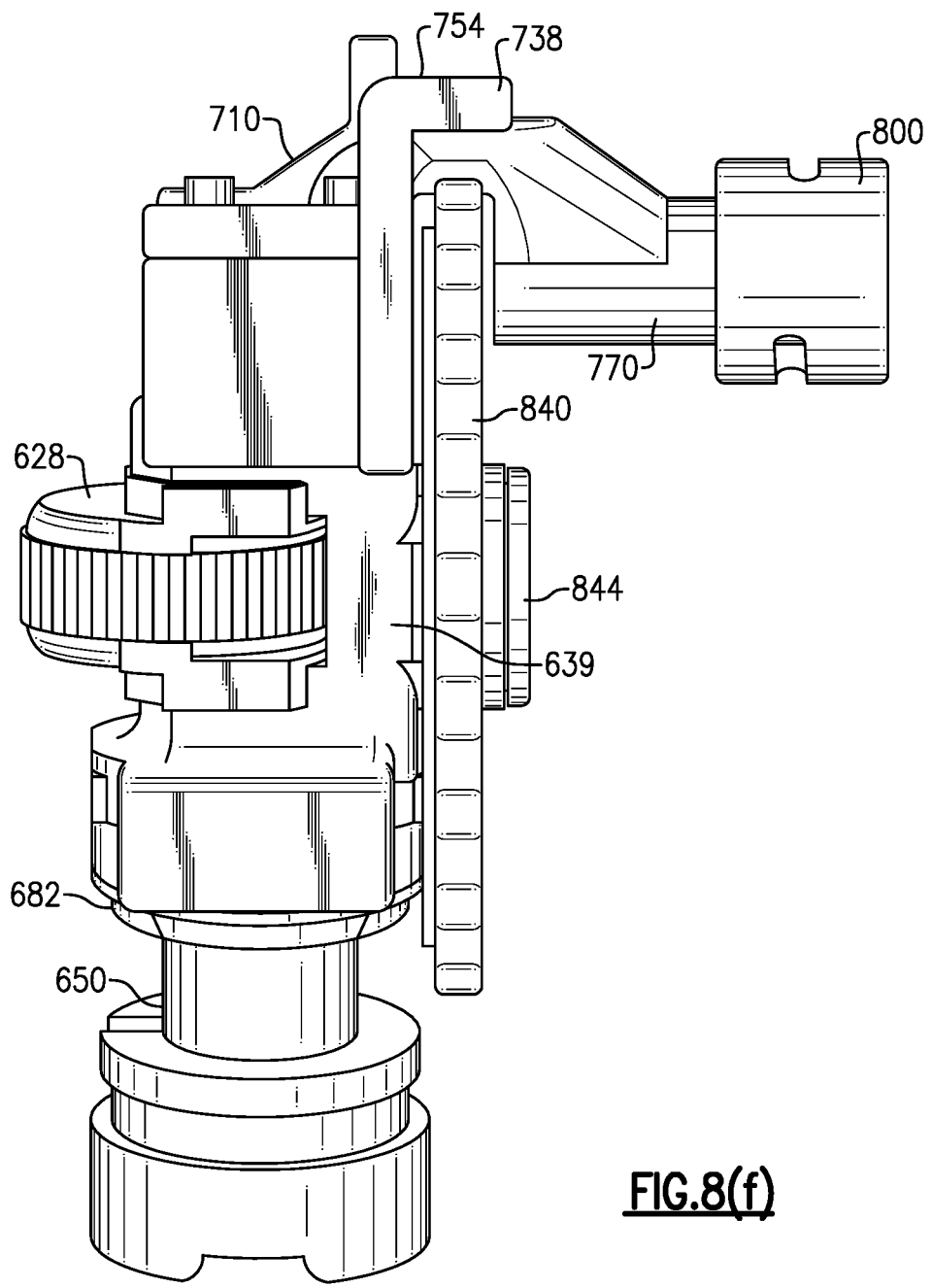

Referring to FIG. 8(e), the diopter wheel 840 is shown prior to attachment, along with a retention cap or hub 844. The diopter wheel 840 includes a center through aperture 842 that is aligned with a lateral cavity 699 formed in the intermediate portion 637 of the assembly support member 628. The hub 844 is engageable with to extend through the aperture 842 and into the cavity 699 to retain the wheel 840, as shown in FIG. 8(f). In this embodiment, the outer periphery 846 of the diopter wheel 840 is caused to extend into the raised second section 754 of the viewing assembly 710 and into contact with the detent 764, which is held in place by the thin metal sheet 810, acting as a biasing spring.

The illumination assembly 610 and optical assembly 710 according to this instrument design does not require fasteners, wherein all of the components can be assembled based on a series of interconnecting fits between the various components.

Referring to FIGS. 9(a)-10(b) and according to another embodiment, the preceding illumination assembly can be used with an existing viewing assembly 610, as would be found, for example, in conjunction with the ophthalmic instrument 200 of FIG. 2.

Figure 9A:
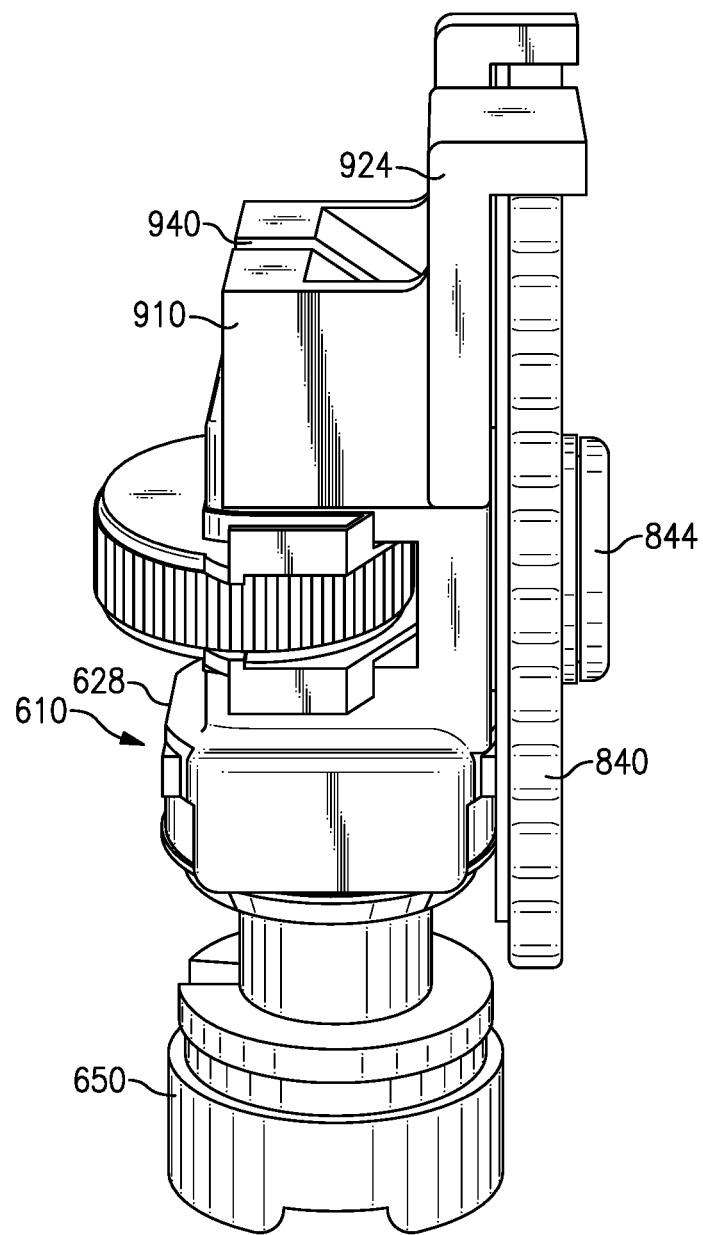
FIGS. 9(a)-9(c) depict partial views of a medical diagnostic instrument made in accordance with yet another embodiment.
Figure 9B:
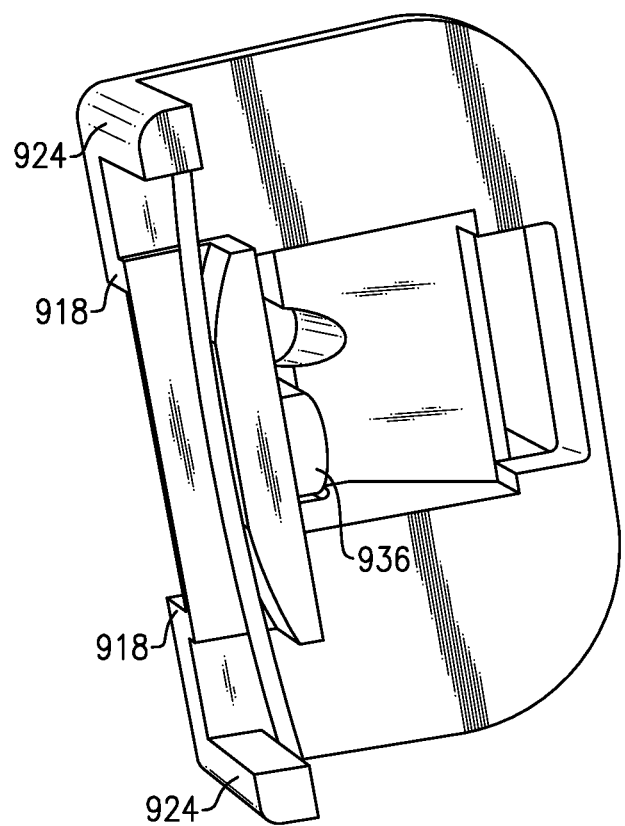
Figure 9C:
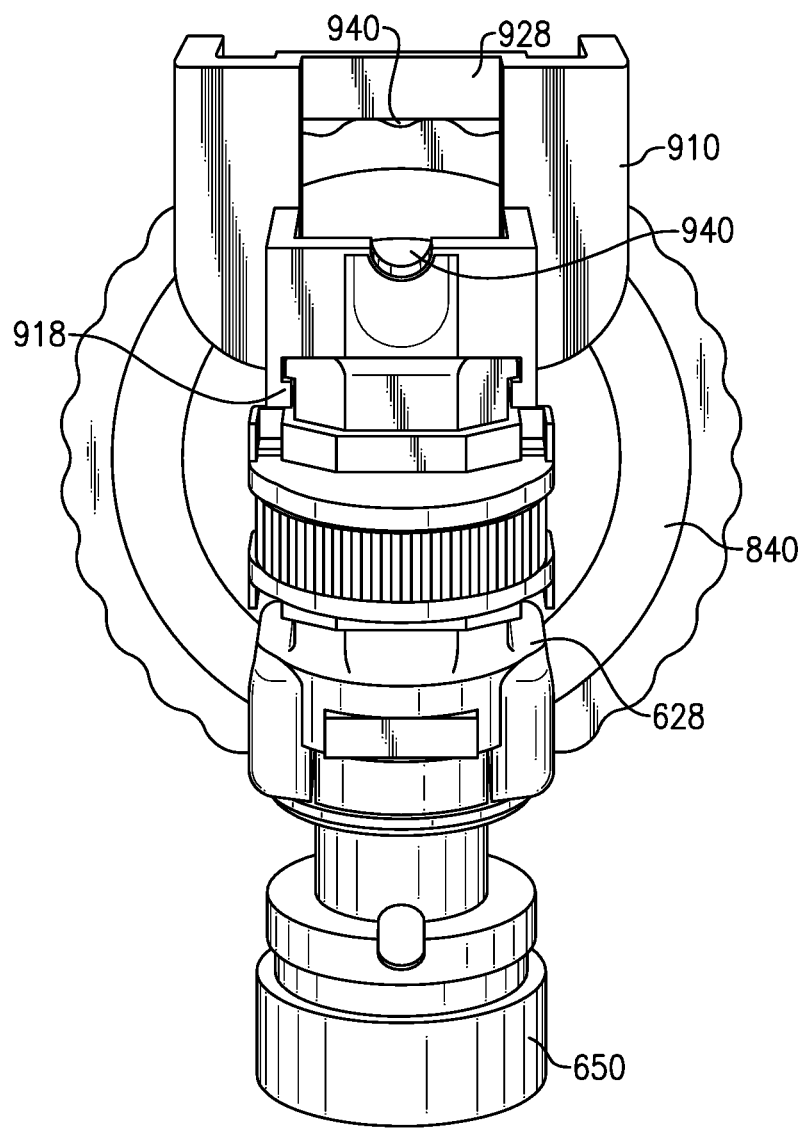

A partially assembled version is shown in FIGS. 9(b) and 9(c), wherein the illumination assembly 610 is identical to that previously described and further including a diopter wheel 840 that is attached to the assembly 610. For purposes of this discussion, similar parts are herein labeled with the same reference numerals for the sake of clarity. The viewing assembly 910 is attached to the upper portion 637 of the illumination assembly 610, the viewing assembly 910 according to this exemplary embodiment comprising a single component that includes a pair of engagement rails 918 to enable the viewing assembly 910 to slidingly engage with the sidewalls 698, FIG. 8(a), of the upper section 637 of the assembly support member 628. The viewing assembly 910 according to this embodiment includes a pair of upwardly extending ears 924, similar to those previously described along with a spring support section 928 having a surface 932 disposed between the spaced ears 924. The surface 932 includes a center opening 936 sized to receive a detent 940 in which the exterior of the surface of the support section 928 supports a thin metallic sheet section 810 whose ends are disposed beneath the ears 924 in order to engage the outer periphery 846 of the supported diopter wheel 840 when rotated. The single component is configured to permit viewing, including a groove disposed on the upper surface.

Figure 10A:
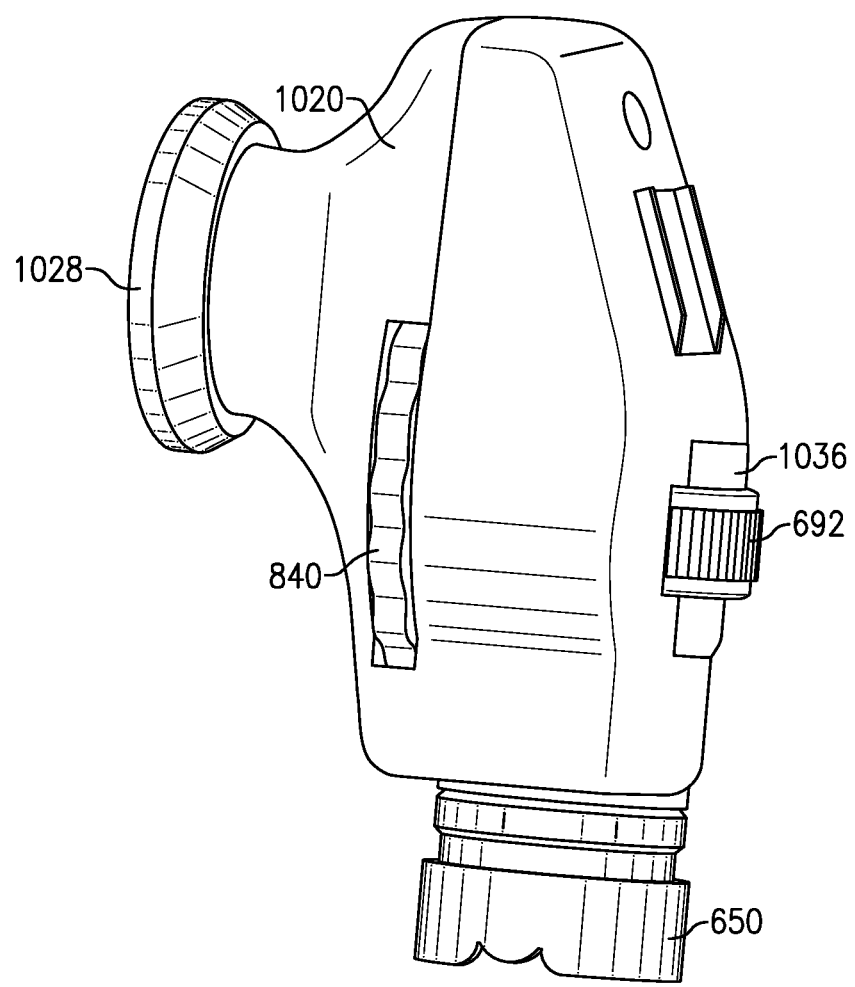
FIGS. 10(a) and 10(b) are perspective views of the assembled medical diagnostic instrument of FIGS. 9(a)-9(c)
Figure 10B:
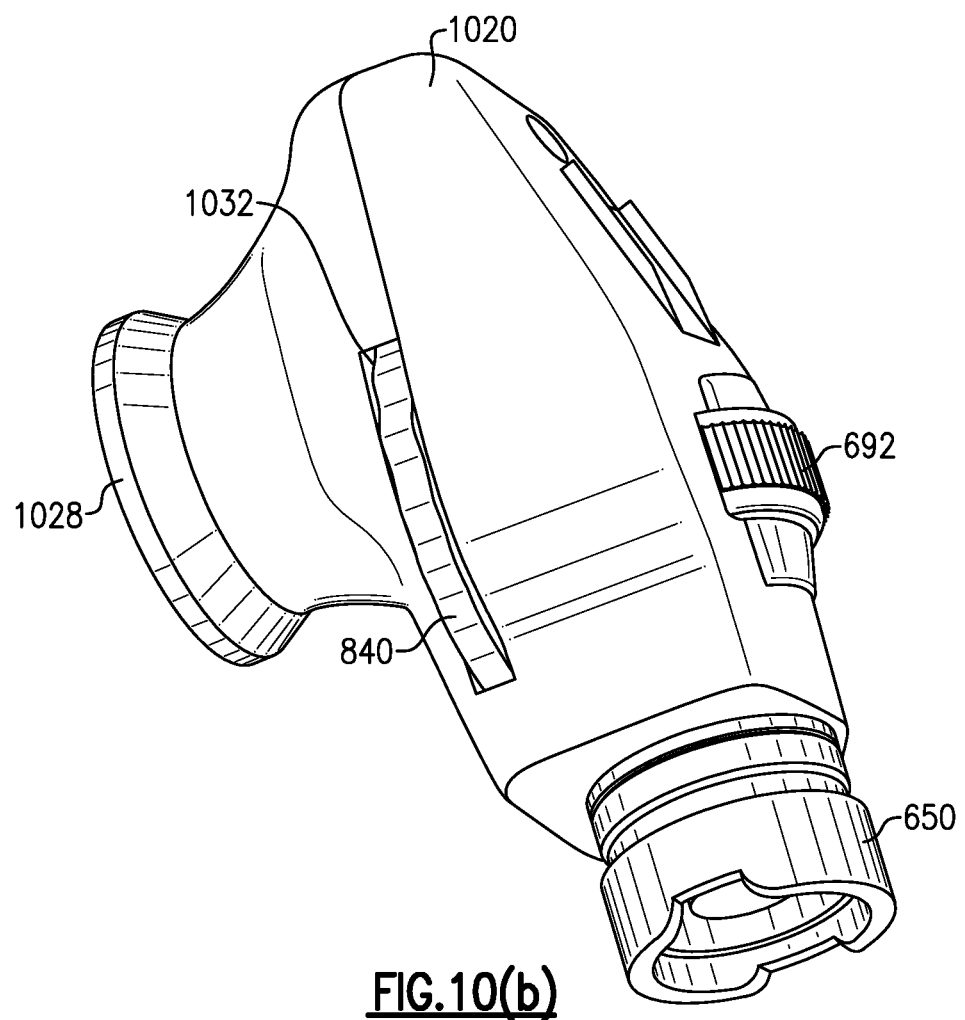

FIGS. 10(a) and 10(b) illustrate a fully assembled version of this latter instrument 1000, including a cover 1020 having slots 1032 and 1036 each sized to enable access to the diopter wheel 840 and aperture wheel 692, as well as a flexible eye cup 1028 at the distal end thereof for contacting the patient.

Figure 12:
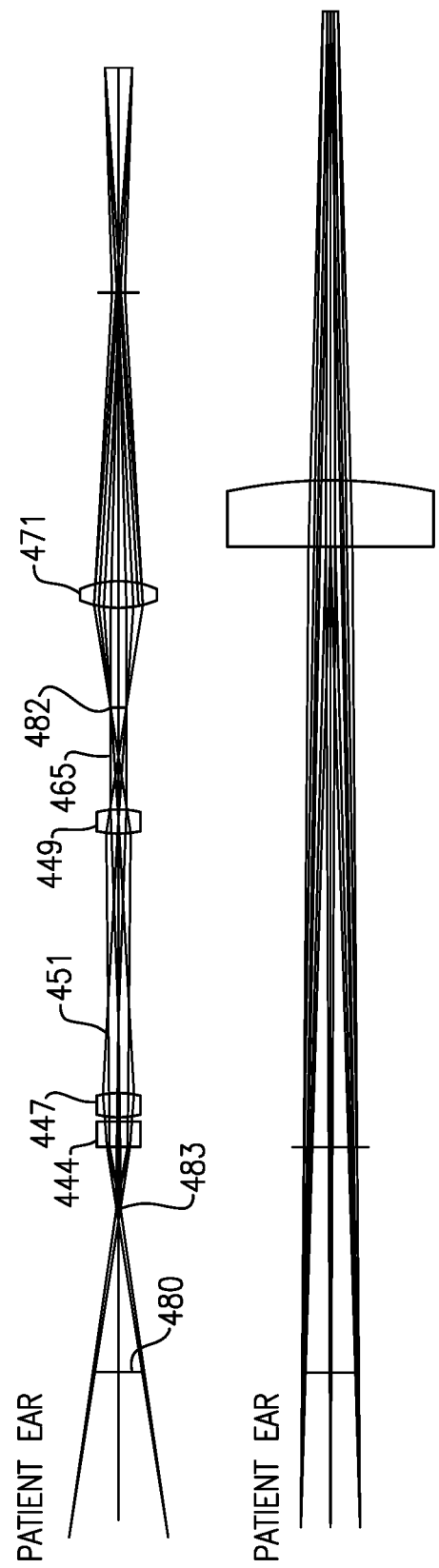
FIG. 12 is a optical layout comparing a prior art otoscope with an otoscope having an optical system in accordance with an embodiment.
Figure 13:
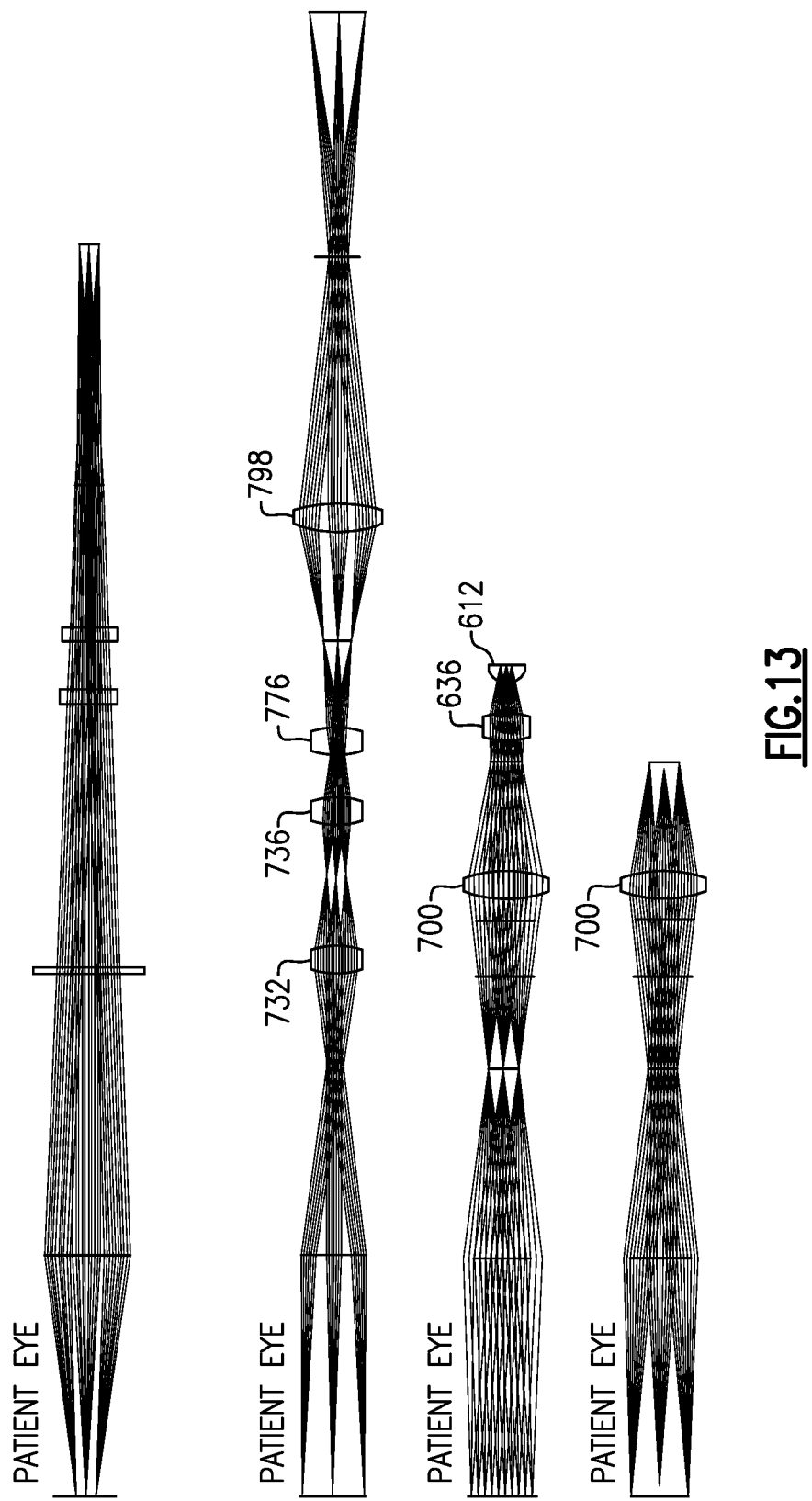
FIG. 13 is an optical layout comparing a prior art ophthalmoscope with an ophthalmoscope configured in accordance with an embodiment.

Functionally, the overall effects provided by the creation of a virtual pupil for each instrument are schematically depicted in FIGS. 12 and 13, comparing the otoscopic and ophthalmic versions described herein with the prior art versions depicted in FIGS. 1 and 2, respectively. With the herein described optical systems, the field of view can be increased from about 5 degrees to about 15 degrees for each device and enables the entire tympanic membrane and a larger portion of the retina to be viewed all at once by the caregiver by an otoscope and ophthalmoscope, respectively.

Another illustration of the overall benefit of the herein described invention is shown comparatively with reference to FIG. 14 between a prior art instrument 1100 having a distance D1 between the eye of the patient 1104 and that of the clinician 1108 and a field of view based on this distance. In the instrument 1150 and creating a "virtual eye" 1158 as previously described the field of view is significantly increased based on the shorter distance between the virtual eye 1158 and that of the patient 1104. The foregoing advantage is provided in spite of the overall increase in thickness of the instrument 1150, in which the creation of an entrance pupil (or "virtual eye") reduces the effective working distance between the eye of the caregiver and the patient by negating the thickness of the instrument to permit the extended field of view and using a direct ophthalmoscope.

PARTS LIST FOR FIGS. 1-14

100 instrument (otoscope)
104 instrument head
108 distal end, instrument head
112 proximal end, instrument head
115 hollow interior
124 distal insertion portion
126 slot
128 distal opening
130 magnifying optic or window
132 bayonet connector
200 instrument (ophthalmoscope)
204 instrument head
205 distal end
207 proximal end
214 bayonet connector
220 diopter wheel
226 aperture wheel
228 sliding switch
400 instrument
404 instrument head
406 distal end
408 proximal end
409 insufflation port 411 illumination connector
413 tip attachment and retention mechanism
416 conical insertion portion
419 actuator knob
420 inner former
423 lower portion
427 opening
428 cover
430 optics assembly
432 housing
434 distal section, housing
435 intermediate section, housing
437 proximal section, housing
439 distal opening
441 proximal opening
444 plano window
447 objective lens
449 relay lens
451 field stop
453 first spacer
454 distal section
456 proximal section
457 intermediate section
459 aperture, narrowed
461 O-rings
463 second spacer
465 field stop
467 peripheral grooves
469 O-ring
471 eyepiece lens
473 retaining cap
475 distal open end
477 annular slots
479 exterior engagement features
480 image
481 proximal viewing opening
482 image plane
483 entrance pupil
540 optical module
544 housing
546 distal end opening
548 proximal end opening
600 instrument, medical diagnostic
610 illumination assembly
612 LED
614 circuit board
616 spacer
618 through aperture, spacer
620 lower flange
622 O-ring
624 curved light pipe
625 slot
626 bottom surface
627 portion of light pipe
628 assembly support member
629 recess
630 lower portion, assembly support member
631 external notch
634 aperture
636 lens element
637 upper portion, assembly support member
638 slot
639 intermediate portion, assembly support member
642 projecting leg portions
644 recess
646 engagement rails
650 illumination connector
654 upper portion, illumination connector
656 intermediate portion, illumination connector
658 lower portion, illumination connector
660 axial through opening
664 insulator
667 lower portion, insulator
670 center conductor
673 axial contacting end
677 curved portions
678 flats
679 curved portions, assembly support member
682 spring clip
686 reticle wheel assembly
688 upper engagement portion, wheel assembly
690 lower engagement portion, wheel assembly
692 aperture wheel
696 through aperture
698 sidewalls, upper portion
699 cavity
700 reticle lens
704 prismatic member
704A prismatic member
706 receiving cavity
710 optical or viewing assembly
712 housing
716 lower or bottom portion
720 upper or top portion
724 top surface
728 semi-circular groove
730 ears
732 first lens
734 vertical portion
736 second lens
738 transverse portion
742 posts
744 holes
750 first portion
754 second portion
756 raised surface
760 center slot
764 detent
766 third portion
770 tubular portion
776 relay lens
780 lens carrier
784 O-ring
790 spacer
794 field stop
798 eyepiece lens
800 retaining cap
802 open distal end
804 plano window
806 annular slots, cap
810 thin metal sheet
840 diopter wheel
842 center aperture
844 hub
846 outer periphery, diopter wheel
850 spaced rail portions
910 viewing assembly
918 engagement rail portions
924 ears
928 support section
932 surface
936 center opening
940 groove
1000 instrument 1020 cover
1028 eye cup
1032 slot, cover
1100 instrument
1104 patient eye
1108 clinician eye
1150 instrument
1158 virtual eye It will be apparent that other modifications and variations of the foregoing exemplary embodiments will be understood from the foregoing description as well as the following claims.

The invention claimed is:

1. A method for illuminating a medical target of interest using a handheld medical diagnostic instrument, the method comprising:
   providing an illumination assembly housing retaining a light source within a handle portion of the medical diagnostic instrument, the illumination assembly housing including an upper portion, a recessed intermediate portion, and a lower portion, and in which the light source is retained in the lower portion of the illumination assembly housing;
   providing an illumination relay lens within the illumination assembly housing and aligned with the light source along an illumination axis;
   providing an aperture wheel assembly within the recessed intermediate portion of the illumination assembly housing, the aperture wheel assembly comprising a rotatable wheel having a plurality of variably sized apertures that can be selectively moved into alignment with the light source along the illumination axis, wherein the aperture wheel assembly is fitted in interlocking fashion within the recessed intermediate portion; and
   providing a mirror assembly aligned with the illumination relay lens and the light source along the illumination axis, the mirror assembly being configured for directing light from the light source toward the medical target.

2. The method according to claim 1, further comprising:
   providing at least one electrical contact disposed within the lower portion of the illumination assembly housing and connecting the at least one electrical contact to the light source.

3. The method according to claim 1, further comprising:
   disposing the illumination assembly housing beneath an optical assembly within the medical diagnostic instrument and transverse to an optical axis of the optical assembly.

4. The method according to claim 3, further comprising:
   disposing the extending portion of the at least one electrical contact in relation to a power source of the medical diagnostic instrument.

5. The method according to claim 3, further comprising:
   disposing the mirror assembly above the optical assembly within the medical diagnostic instrument; and
   aligning the mirror assembly to direct reflected light from the light source along the optical axis to the medical target.

6. The method according to claim 3, in which the medical diagnostic instrument is an ophthalmoscope.

7. An illumination assembly for a medical diagnostic instrument having an instrument head and an instrument handle downwardly extending from the instrument head, the illumination assembly comprising:
   an illumination assembly housing disposed within the instrument handle, the illumination assembly housing having an upper section, a recessed intermediate section and a lower section;
   an aperture wheel mounted for rotation within the recessed intermediate section of the illumination assembly housing, the aperture wheel including a plurality of circumferentially spaced apertures aligned with an illumination axis in which the aperture wheel is disposed on a wheel assembly sized to fit in interlocking fashion within the recessed intermediate section;
   a light source disposed within the lower portion of the illumination assembly housing; and
   an electrical contact connected to the light source, at least a portion of the electrical contact extending outward from the lower section of the illumination assembly housing.

8. The illumination assembly according to claim 7, further comprising:
   an illumination relay lens disposed in the upper section of the illumination assembly housing and aligned with the light source along an illumination axis.

9. The illumination assembly according to claim 7, in which upper and lower engagement portions of the wheel assembly include engagement rails configured to engage sidewalls of the upper and lower portions of the illumination assembly housing.

10. The illumination assembly according to claim 7, in which the medical diagnostic instrument includes an optical assembly, in which the illumination assembly housing is disposed below and transverse to an optical axis of the optical assembly.

11. The illumination assembly according to claim 10, in which the mirror assembly is disposed above the illumination assembly housing and includes an angled reflective surface aligned to direct reflected light from the light source toward a medical target.

12. The illumination assembly according to claim 7, in which the electrical contact is configured to contact a power source of the medical diagnostic instrument.

13. The illumination assembly according to claim 12, in which the electrical contact pin is disposed within an illuminator connector attached to the lower portion of the illumination assembly housing.

14. The illumination assembly according to claim 13, in which the electrical contact is a pin, the illuminator connector retaining an insulator having an opening that retains the electrical contact pin.

15. The illumination assembly according to claim 7, in which the medical diagnostic instrument is an ophthalmoscope.

16. The illumination assembly according to claim 7, further comprising an illuminator connector, wherein the lower portion of the illumination assembly housing includes a recess disposed between a pair of extending leg portions and in which an upper portion of the illuminator connector is shaped and configured to releasably engage the lower portion of the illumination assembly housing in an interlocking manner, wherein the upper portion of the illuminator connector includes a pair of diametrically opposed curved portions and a pair of flats spaced to fit between the extending leg portions.

17. The illumination assembly according to claim 16, further comprising a spacer fitted within a recess formed in the lower portion of the illumination assembly housing relative to an aperture that retains a lens element, wherein the light source and a circuit board are retained between the spacer and a center conductor of the illumination connector.

\* \* \* \* \*